(12) United States Patent
Alvarez et al.

(10) Patent No.: US 10,744,035 B2
(45) Date of Patent: Aug. 18, 2020

(54) METHODS FOR ROBOTIC ASSISTED CATARACT SURGERY

(71) Applicant: Auris Health, Inc., Redwood City, CA (US)

(72) Inventors: Jeffery B. Alvarez, Redwood City, CA (US); Greg Kintz, Santa Cruz, CA (US); David Mintz, Mountain View, CA (US); Serena Wong, Menlo Park, CA (US)

(73) Assignee: Auris Health, Inc., Redwood City, CA (US)

( * ) Notice: Subject to any disclaimer, the term of this patent is extended or adjusted under 35 U.S.C. 154(b) by 250 days.

(21) Appl. No.: 14/301,871

(22) Filed: Jun. 11, 2014

(65) Prior Publication Data

US 2014/0364870 A1    Dec. 11, 2014

Related U.S. Application Data

(60) Provisional application No. 61/833,835, filed on Jun. 11, 2013.

(51) Int. Cl.
*A61F 9/008* (2006.01)
*A61B 34/30* (2016.01)
(Continued)

(52) U.S. Cl.
CPC ............ *A61F 9/008* (2013.01); *A61B 34/30* (2016.02); *A61B 34/37* (2016.02);
(Continued)

(58) Field of Classification Search
CPC .. A61F 9/007; A61F 9/00709; A61F 9/00736; A61F 9/00745; A61F 9/00754;
(Continued)

(56) References Cited

U.S. PATENT DOCUMENTS 3,763,860 A   10/1973 Clarke
4,040,413 A    8/1977 Ohshiro
(Continued)

FOREIGN PATENT DOCUMENTS

EP   1 321 106    6/2003
EP   1 849 423   10/2007
(Continued)

OTHER PUBLICATIONS

U.S. Appl. No. 14/196,953, filed Mar. 4, 2014, Alvarez et al.
(Continued)

*Primary Examiner* — Christopher L Templeton
(74) *Attorney, Agent, or Firm* — Knobbe, Martens, Olson & Bear, LLP

(57) ABSTRACT

Systems and processes for facilitating the removal of cataract material with a robotically assisted tool with laser, irrigation capabilities, aspiration capabilities. Tool guidance systems that make use of vision technologies, including optical coherence tomography (OCT), white light imaging, and structured light imaging. Emulsification patterns optimized to minimize risk to the patient and reduce procedure time. Robotic tools with articulation capabilities that allow for precise control during capsulorhexis and emulsification procedures. Robotic instrument drive mechanisms combined with pumps, flow meters, and valves regulate and control irrigation and aspiration functionalities during robotic ophthalmologic procedures.

19 Claims, 31 Drawing Sheets

(51) Int. Cl.
*A61F 9/007* (2006.01)
*A61B 34/37* (2016.01)

(52) U.S. Cl.
CPC .. *A61F 9/00736* (2013.01); *A61F 2009/0087* (2013.01); *A61F 2009/00851* (2013.01); *A61F 2009/00887* (2013.01); *A61F 2009/00889* (2013.01)

(58) Field of Classification Search
CPC ............ A61F 9/008; A61F 9/00763; A61F 2009/00846; A61F 2009/00844; A61F 2009/00885; A61F 2009/00889; A61F 2009/00887; A61F 2009/0087; A61F 2009/00851; A61M 25/0133; A61M 25/0147; A61B 2017/00323; A61B 2017/00336; A61B 2017/003; A61B 2017/00318; A61B 2017/00327
See application file for complete search history.

(56) References Cited

U.S. PATENT DOCUMENTS

| | | | |
|---|---|---|---|
| 4,198,960 A | 4/1980 | Utsugi | |
| 4,470,407 A | 9/1984 | Hussein | |
| 4,532,935 A | 8/1985 | Wang et al. | |
| 4,597,388 A | 7/1986 | Koziol et al. | |
| 4,685,458 A | 8/1987 | Leckrone | |
| 4,747,405 A | 5/1988 | Leckrone | |
| 4,898,574 A | 2/1990 | Uchiyama et al. | |
| 4,905,673 A | 3/1990 | Pimiskern | |
| 4,983,165 A | 1/1991 | Loiterman | |
| 5,029,574 A | 7/1991 | Shimamura et al. | |
| 5,085,659 A | 2/1992 | Rydell | |
| 5,196,023 A | 3/1993 | Martin | |
| 5,217,465 A * | 6/1993 | Steppe | A61M 1/008 604/19 |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,425,735 A | 6/1995 | Rosen et al. | |
| 5,431,649 A | 7/1995 | Mulier et al. | |
| 5,441,485 A | 8/1995 | Peters | |
| 5,449,356 A * | 9/1995 | Walbrink | A61B 18/1482 606/37 |
| 5,450,843 A | 9/1995 | Moll et al. | |
| 5,472,406 A | 12/1995 | De La Torre et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,520,684 A | 5/1996 | Imran | |
| 5,545,170 A | 8/1996 | Hart | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,662,590 A | 9/1997 | De La Torre et al. | |
| 5,695,461 A | 12/1997 | Schaible | |
| 5,695,500 A | 12/1997 | Taylor et al. | |
| 5,697,949 A | 12/1997 | Giurtino et al. | |
| 5,710,870 A | 1/1998 | Ohm | |
| 5,716,325 A | 2/1998 | Bonutti | |
| 5,788,667 A | 8/1998 | Stoller | |
| 5,792,165 A | 8/1998 | Klieman | |
| 5,797,900 A | 8/1998 | Madhani | |
| 5,810,770 A | 9/1998 | Chin et al. | |
| 5,893,869 A * | 4/1999 | Barnhart | A61F 2/01 604/264 |
| 5,924,175 A | 7/1999 | Lippitt | |
| 5,989,230 A | 11/1999 | Frassica | |
| 6,033,371 A | 3/2000 | Torre et al. | |
| 6,071,281 A | 6/2000 | Burnside et al. | |
| 6,093,157 A | 7/2000 | Chandrasekaran | |
| 6,120,476 A | 9/2000 | Fung et al. | |
| 6,120,498 A * | 9/2000 | Jani | A61F 9/00802 604/35 |
| 6,156,030 A * | 12/2000 | Neev | A61B 18/20 216/94 |
| 6,174,318 B1 | 1/2001 | Bates et al. | |
| 6,206,903 B1 | 3/2001 | Ramans | |
| 6,183,435 B1 | 6/2001 | Bumbalough et al. | |
| 6,322,557 B1 * | 11/2001 | Nikolaevich | A61F 9/008 606/10 |
| 6,326,616 B1 | 12/2001 | Andrien et al. | |
| 6,375,635 B1 | 4/2002 | Moutafis | |
| 6,394,998 B1 | 5/2002 | Wallace et al. | |
| 6,398,792 B1 | 6/2002 | O'Connor | |
| 6,405,078 B1 | 6/2002 | Moaddeb et al. | |
| 6,406,486 B1 | 6/2002 | De La Torre et al. | |
| 6,436,107 B1 | 8/2002 | Wang et al. | |
| 6,440,061 B1 | 8/2002 | Wenner et al. | |
| 6,508,823 B1 | 1/2003 | Gonon | |
| 6,522,906 B1 | 2/2003 | Salisbury et al. | |
| 6,554,793 B1 | 4/2003 | Pauker et al. | |
| 6,577,891 B1 | 6/2003 | Jaross et al. | |
| 6,638,246 B1 | 10/2003 | Naimark et al. | |
| 6,671,581 B2 | 12/2003 | Niemeyer et al. | |
| 6,676,668 B2 | 1/2004 | Mercereau et al. | |
| 6,685,698 B2 | 2/2004 | Morley et al. | |
| 6,706,050 B1 | 3/2004 | Giannadakis | |
| 6,736,784 B1 | 5/2004 | Menne et al. | |
| 6,763,259 B1 | 7/2004 | Hauger et al. | |
| 7,087,061 B2 | 8/2006 | Chernenko et al. | |
| 7,282,055 B2 | 10/2007 | Tsuruta | |
| 7,344,528 B1 | 3/2008 | Tu et al. | |
| 7,351,193 B2 | 4/2008 | Forman et al. | |
| 7,559,934 B2 | 7/2009 | Teague et al. | |
| 7,725,214 B2 | 5/2010 | Diolaiti | |
| 7,736,356 B2 | 6/2010 | Cooper et al. | |
| 7,883,475 B2 | 2/2011 | Dupont et al. | |
| 7,963,911 B2 | 6/2011 | Turliuc | |
| 7,967,799 B2 | 6/2011 | Boukhny | |
| 8,002,713 B2 | 8/2011 | Heske | |
| 8,038,598 B2 | 10/2011 | Khachi | |
| 8,049,873 B2 | 11/2011 | Hauger et al. | |
| 8,092,397 B2 | 1/2012 | Wallace et al. | |
| 8,187,173 B2 | 5/2012 | Miyoshi | |
| 8,224,484 B2 | 7/2012 | Swarup et al. | |
| 8,257,303 B2 | 9/2012 | Moll et al. | |
| 8,414,564 B2 | 4/2013 | Goldshleger et al. | |
| 8,518,024 B2 | 8/2013 | Williams et al. | |
| 8,523,762 B2 | 9/2013 | Miyamoto et al. | |
| 8,540,748 B2 | 9/2013 | Murphy et al. | |
| 8,652,030 B2 | 2/2014 | Matsuura et al. | |
| 8,820,603 B2 | 9/2014 | Shelton et al. | |
| 8,827,948 B2 | 9/2014 | Romo et al. | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 9,014,851 B2 | 4/2015 | Wong et al. | |
| 9,057,600 B2 | 6/2015 | Walker et al. | |
| 9,138,166 B2 | 9/2015 | Wong et al. | |
| 9,173,713 B2 | 11/2015 | Hart et al. | |
| 9,254,123 B2 | 2/2016 | Alvarez et al. | |
| 9,289,578 B2 | 3/2016 | Walker et al. | |
| 9,345,456 B2 | 5/2016 | Tsonton et al. | |
| 9,460,536 B2 | 10/2016 | Hasegawa et al. | |
| 9,498,291 B2 | 11/2016 | Balaji et al. | |
| 9,504,604 B2 | 11/2016 | Alvarez | |
| 9,532,840 B2 | 1/2017 | Wong et al. | |
| 9,561,083 B2 | 2/2017 | Yu et al. | |
| 9,566,414 B2 | 2/2017 | Wong et al. | |
| 9,592,042 B2 | 3/2017 | Titus | |
| 9,597,152 B2 | 3/2017 | Schaeffer | |

(56) References Cited

U.S. PATENT DOCUMENTS

| | | | |
|---|---|---|---|
| 9,622,827 B2 | 4/2017 | Yu et al. | |
| 9,636,184 B2 | 5/2017 | Lee et al. | |
| 9,710,921 B2 | 7/2017 | Wong et al. | |
| 9,713,509 B2 | 7/2017 | Schuh et al. | |
| 9,727,963 B2 | 8/2017 | Mintz et al. | |
| 9,730,757 B2 | 8/2017 | Brudniok | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,827,061 B2 | 11/2017 | Balaji et al. | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 10,016,900 B1 | 7/2018 | Meyer et al. | |
| 10,022,192 B1 | 7/2018 | Ummalaneni | |
| 10,123,755 B2 | 11/2018 | Walker et al. | |
| 10,136,959 B2 | 11/2018 | Mintz et al. | |
| 10,145,747 B1 | 12/2018 | Lin et al. | |
| 10,159,532 B1 | 12/2018 | Ummalaneni et al. | |
| 10,482,599 B2 | 11/2019 | Mintz et al. | |
| 10,517,692 B2 | 12/2019 | Eyre et al. | |
| 10,524,866 B2 | 1/2020 | Srinivasan | |
| 2002/0019644 A1 | 2/2002 | Hastings | |
| 2002/0111608 A1* | 8/2002 | Baerveldt | A61F 9/00781 606/6 |
| 2002/0111621 A1 | 8/2002 | Wallace et al. | |
| 2003/0004455 A1* | 1/2003 | Kadziauskas | A61F 9/00745 604/27 |
| 2003/0040681 A1 | 2/2003 | Ng et al. | |
| 2003/0065358 A1 | 4/2003 | Frecker | |
| 2003/0109877 A1 | 6/2003 | Morley | |
| 2003/0109889 A1 | 6/2003 | Mercereau | |
| 2003/0158545 A1 | 8/2003 | Hovda et al. | |
| 2003/0208189 A1* | 11/2003 | Payman | A61F 9/008 606/5 |
| 2004/0030349 A1 | 2/2004 | Boukhny | |
| 2004/0135733 A1 | 7/2004 | Chou et al. | |
| 2004/0143253 A1 | 7/2004 | Vanney | |
| 2004/0153093 A1* | 8/2004 | Donovan | A61F 9/00736 606/108 |
| 2004/0158261 A1 | 8/2004 | Vu | |
| 2004/0186349 A1 | 9/2004 | Ewers | |
| 2004/0193146 A1 | 9/2004 | Lee et al. | |
| 2004/0210116 A1 | 10/2004 | Nakao | |
| 2005/0033270 A1 | 2/2005 | Ramans et al. | |
| 2005/0054900 A1* | 3/2005 | Mawn | A61B 1/3132 600/156 |
| 2005/0070844 A1 | 3/2005 | Chow et al. | |
| 2005/0159645 A1 | 7/2005 | Bertolero | |
| 2005/0240178 A1 | 10/2005 | Morley et al. | |
| 2005/0261705 A1 | 11/2005 | Gist | |
| 2006/0015133 A1 | 1/2006 | Grayzel | |
| 2006/0058813 A1 | 3/2006 | Teague | |
| 2006/0116693 A1 | 6/2006 | Weisenburgh | |
| 2006/0135963 A1 | 6/2006 | Kick | |
| 2006/0156875 A1 | 7/2006 | McRury et al. | |
| 2006/0189891 A1 | 8/2006 | Waxman et al. | |
| 2006/0229598 A1 | 10/2006 | Shadduck | |
| 2007/0016164 A1 | 1/2007 | Dudney et al. | |
| 2007/0027443 A1* | 2/2007 | Rose | A61C 1/088 606/16 |
| 2007/0027534 A1 | 2/2007 | Bergheim | |
| 2007/0032906 A1 | 2/2007 | Sutherland et al. | |
| 2007/0106304 A1 | 5/2007 | Hammack | |
| 2007/0135763 A1 | 6/2007 | Musbach et al. | |
| 2007/0135803 A1* | 6/2007 | Belson | A61B 1/00154 606/1 |
| 2007/0208375 A1 | 9/2007 | Nishizawa | |
| 2007/0213668 A1 | 9/2007 | Spitz | |
| 2007/0239178 A1 | 10/2007 | Weitzner et al. | |
| 2007/0250111 A1 | 10/2007 | Lu | |
| 2007/0299427 A1 | 12/2007 | Yeung et al. | |
| 2008/0015566 A1 | 1/2008 | Livneh | |
| 2008/0021440 A1 | 1/2008 | Solomon | |
| 2008/0033467 A1 | 2/2008 | Miyamoto et al. | |
| 2008/0046122 A1 | 2/2008 | Manzo et al. | |
| 2008/0065109 A1 | 3/2008 | Larkin | |
| 2008/0065111 A1 | 3/2008 | Blumenkranz | |
| 2008/0097293 A1 | 4/2008 | Chin et al. | |
| 2008/0114341 A1 | 5/2008 | Thyzel | |
| 2008/0125698 A1 | 5/2008 | Greg et al. | |
| 2008/0177285 A1 | 7/2008 | Brock et al. | |
| 2008/0187101 A1 | 8/2008 | Gertner | |
| 2008/0196533 A1 | 8/2008 | Bergamasco | |
| 2008/0228104 A1 | 9/2008 | Uber et al. | |
| 2009/0012507 A1* | 1/2009 | Culbertson | A61F 2/16 606/6 |
| 2009/0030446 A1 | 1/2009 | Measamer | |
| 2009/0036900 A1 | 2/2009 | Moll | |
| 2009/0043305 A1 | 2/2009 | Brodbeck | |
| 2009/0062602 A1 | 3/2009 | Rosenberg et al. | |
| 2009/0082634 A1 | 3/2009 | Kathrani et al. | |
| 2009/0088774 A1 | 4/2009 | Swarup et al. | |
| 2009/0105723 A1 | 4/2009 | Dillinger | |
| 2009/0131885 A1* | 5/2009 | Akahoshi | A61F 9/00736 604/272 |
| 2009/0161827 A1* | 6/2009 | Gertner | A61F 9/008 378/65 |
| 2009/0171271 A1 | 7/2009 | Webster et al. | |
| 2009/0248041 A1 | 10/2009 | Williams et al. | |
| 2009/0248043 A1 | 10/2009 | Tierney et al. | |
| 2009/0264878 A1 | 10/2009 | Carmel et al. | |
| 2009/0268015 A1 | 10/2009 | Scott et al. | |
| 2009/0270760 A1 | 10/2009 | Leimbach et al. | |
| 2009/0287188 A1 | 11/2009 | Golden et al. | |
| 2009/0299352 A1* | 12/2009 | Zerfas | A61B 1/00165 606/15 |
| 2009/0312768 A1 | 12/2009 | Hawkins et al. | |
| 2009/0326322 A1 | 12/2009 | Diolaiti | |
| 2010/0004642 A1* | 1/2010 | Lumpkin | A61B 18/22 606/4 |
| 2010/0010504 A1* | 1/2010 | Simaan | A61B 90/16 606/130 |
| 2010/0011901 A1 | 1/2010 | Burbank | |
| 2010/0036294 A1 | 2/2010 | Mantell et al. | |
| 2010/0073150 A1 | 3/2010 | Olson et al. | |
| 2010/0082017 A1* | 4/2010 | Zickler | A61F 2/16 606/4 |
| 2010/0179632 A1 | 7/2010 | Bruszewski et al. | |
| 2010/0204605 A1 | 8/2010 | Blakley | |
| 2010/0204646 A1 | 8/2010 | Plicchi et al. | |
| 2010/0217235 A1 | 8/2010 | Thorstenson | |
| 2010/0225209 A1 | 9/2010 | Goldberg | |
| 2010/0228191 A1 | 9/2010 | Alvarez et al. | |
| 2010/0228249 A1 | 9/2010 | Mohr | |
| 2010/0280320 A1 | 11/2010 | Alvarez et al. | |
| 2010/0280525 A1 | 11/2010 | Alvarez et al. | |
| 2010/0312141 A1 | 12/2010 | Keast et al. | |
| 2010/0331858 A1* | 12/2010 | Simaan | A61F 2/82 606/130 |
| 2011/0009779 A1 | 1/2011 | Romano et al. | |
| 2011/0015483 A1 | 1/2011 | Barbagli | |
| 2011/0015648 A1 | 1/2011 | Alvarez et al. | |
| 2011/0028887 A1 | 2/2011 | Fischer et al. | |
| 2011/0040404 A1 | 2/2011 | Diolaiti et al. | |
| 2011/0046441 A1 | 2/2011 | Wiltshire et al. | |
| 2011/0071541 A1 | 3/2011 | Prisco et al. | |
| 2011/0071543 A1 | 3/2011 | Prisco et al. | |
| 2011/0106102 A1 | 5/2011 | Balicki et al. | |
| 2011/0106146 A1 | 5/2011 | Jeong | |
| 2011/0125165 A1* | 5/2011 | Simaan | A61F 9/007 606/130 |
| 2011/0152880 A1* | 6/2011 | Alvarez | A61M 25/0138 606/130 |
| 2011/0160713 A1 | 6/2011 | Neuberger | |
| 2011/0167611 A1 | 7/2011 | Williams | |
| 2011/0213362 A1 | 9/2011 | Cunningham | |
| 2011/0224660 A1 | 9/2011 | Neuberger et al. | |

(56) References Cited

U.S. PATENT DOCUMENTS

| | | |
|---|---|---|
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0306836 A1 | 12/2011 | Ohline et al. |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0172786 A1 | 7/2012 | MacKool |
| 2012/0209315 A1 | 8/2012 | Amat |
| 2012/0232342 A1 | 9/2012 | Reydel |
| 2012/0253332 A1* | 10/2012 | Moll ............... A61G 7/0503 606/4 |
| 2012/0259320 A1* | 10/2012 | Loesel ............. A61F 9/00825 606/5 |
| 2012/0283747 A1 | 11/2012 | Popovic |
| 2012/0296318 A1* | 11/2012 | Wellhofer ......... A61F 9/00802 606/4 |
| 2013/0006144 A1 | 1/2013 | Clancy |
| 2013/0030363 A1 | 1/2013 | Wong et al. |
| 2013/0035537 A1 | 2/2013 | Wallace et al. |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1* | 4/2013 | Boctor ............... A61B 5/0095 600/424 |
| 2013/0096574 A1* | 4/2013 | Kang ............... A61B 17/1622 606/130 |
| 2013/0110042 A1 | 5/2013 | Humphreys |
| 2013/0110107 A1 | 5/2013 | Smith et al. |
| 2013/0116714 A1 | 5/2013 | Adams et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1* | 8/2013 | Hickenbotham ....... A61F 9/008 606/5 |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1* | 12/2013 | Brown ............... A61B 18/22 606/15 |
| 2014/0005681 A1 | 1/2014 | Gee et al. |
| 2014/0012276 A1 | 1/2014 | Alvarez |
| 2014/0039681 A1 | 2/2014 | Bowling |
| 2014/0046308 A1* | 2/2014 | Bischoff ............ A61B 18/201 606/4 |
| 2014/0051985 A1 | 2/2014 | Fan |
| 2014/0058365 A1* | 2/2014 | Bille ............... A61F 9/00827 606/5 |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1* | 7/2014 | Ianchulev ......... A61F 9/00736 606/6 |
| 2014/0194905 A1 | 7/2014 | Kappel |
| 2014/0243849 A1 | 8/2014 | Saglam |
| 2014/0257334 A1 | 9/2014 | Wong et al. |
| 2014/0264081 A1 | 9/2014 | Walker et al. |
| 2014/0275956 A1 | 9/2014 | Fan |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276646 A1 | 9/2014 | Wong et al. |
| 2014/0276723 A1 | 9/2014 | Parihar |
| 2014/0276933 A1 | 9/2014 | Hart et al. |
| 2014/0276934 A1 | 9/2014 | Balaji et al. |
| 2014/0276937 A1 | 9/2014 | Wong et al. |
| 2014/0276956 A1 | 9/2014 | Crainich |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0127045 A1 | 5/2015 | Prestel |
| 2015/0164522 A1 | 6/2015 | Budiman |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0201917 A1 | 7/2015 | Snow |
| 2015/0202085 A1* | 7/2015 | Lemonis ............ A61F 9/00825 606/5 |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0151122 A1 | 6/2016 | Alvarez et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0202053 A1 | 7/2016 | Walker et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0065356 A1 | 3/2017 | Balaji et al. |
| 2017/0065364 A1 | 3/2017 | Schuh et al. |
| 2017/0065365 A1 | 3/2017 | Schuh |
| 2017/0095234 A1 | 4/2017 | Prisco et al. |
| 2017/0095295 A1 | 4/2017 | Overmyer |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0113019 A1 | 4/2017 | Wong et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151027 A1 | 6/2017 | Walker et al. |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0055583 A1 | 3/2018 | Schuh et al. |
| 2018/0177383 A1 | 6/2018 | Noonan et al. |
| 2018/0177556 A1 | 6/2018 | Noonan et al. |

(56) References Cited

U.S. PATENT DOCUMENTS

| | | |
|---|---|---|
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |

FOREIGN PATENT DOCUMENTS

| | | | | |
|---|---|---|---|---|
| JP | H09224951 A | | 9/1997 | |
| JP | 2005-270464 | | 10/2005 | |
| WO | WO 92/14411 A1 | | 9/1992 | |
| WO | WO 03/096871 A2 | | 11/2003 | |
| WO | WO 2004/105849 A1 | | 12/2004 | |
| WO | WO 2011/161218 A1 | | 12/2011 | |
| WO | WO 2013/107468 | * | 7/2013 | ............ A61F 9/008 |
| WO | WO 13/130895 | | 9/2013 | |
| WO | WO 17/114855 | | 7/2017 | |
| WO | WO 18/069679 | | 4/2018 | |

OTHER PUBLICATIONS

U.S. Appl. No. 14/201,610, filed Mar. 7, 2014, Romo.
U.S. Appl. No. 14/458,042, filed Aug. 12, 2014, Kintz.
U.S. Appl. No. 14/479,095, filed Sep. 5, 2014, Romo et al.
U.S. Appl. No. 14/523,760, filed Oct. 24, 2014, Alvarez et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
U.S. Appl. No. 14/541,373, filed Nov. 14, 2014, Romo et al.
U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
Office action dated Oct. 7, 2014 for U.S. Appl. No. 13/711,440.
European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.

* cited by examiner

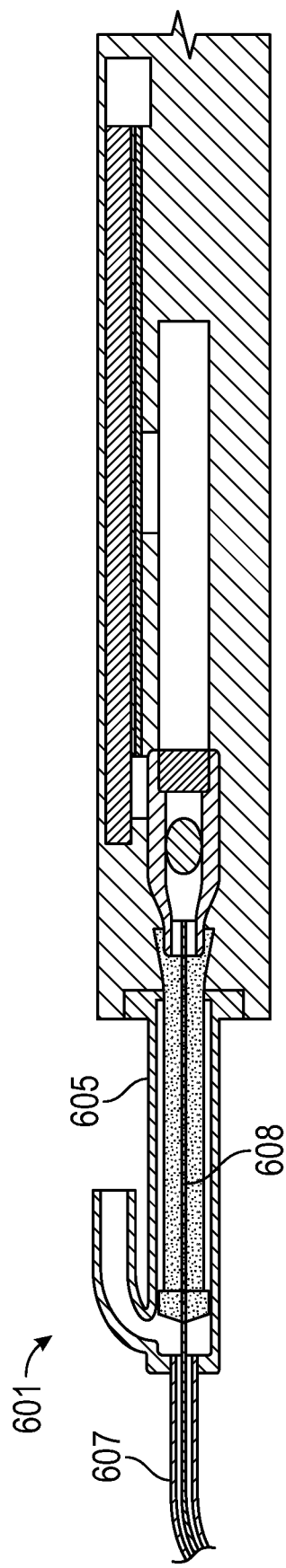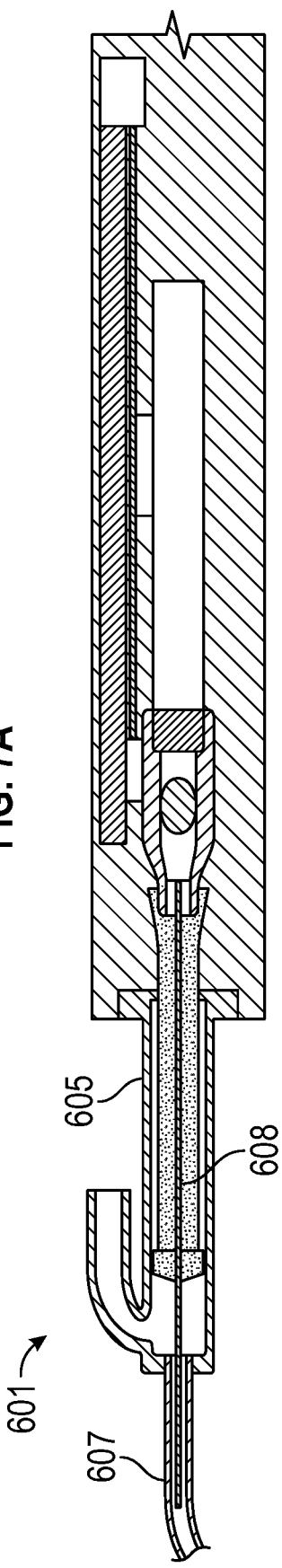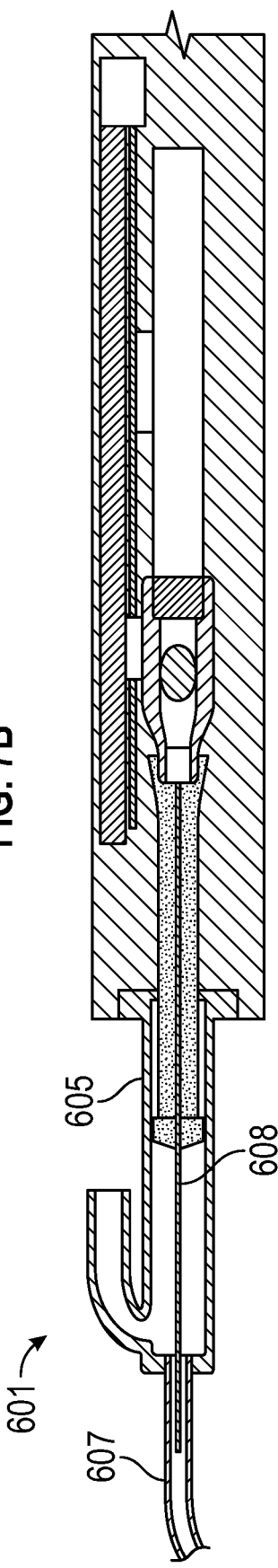

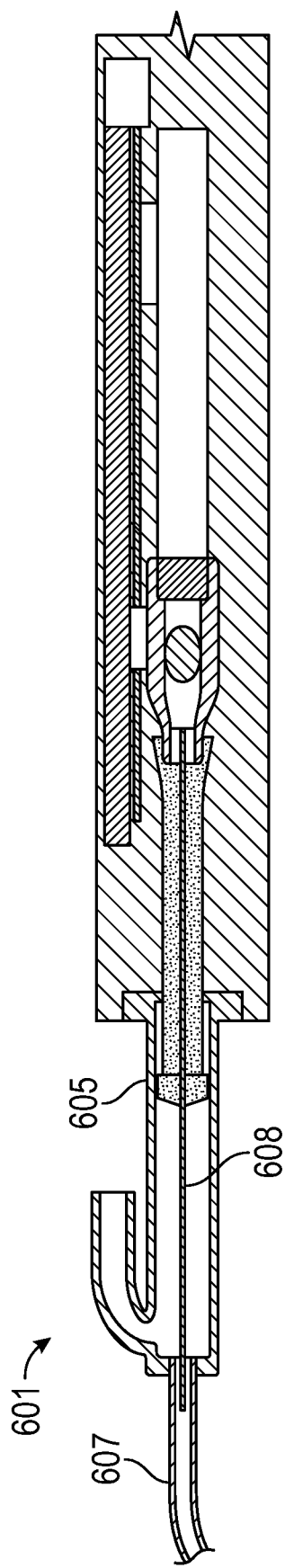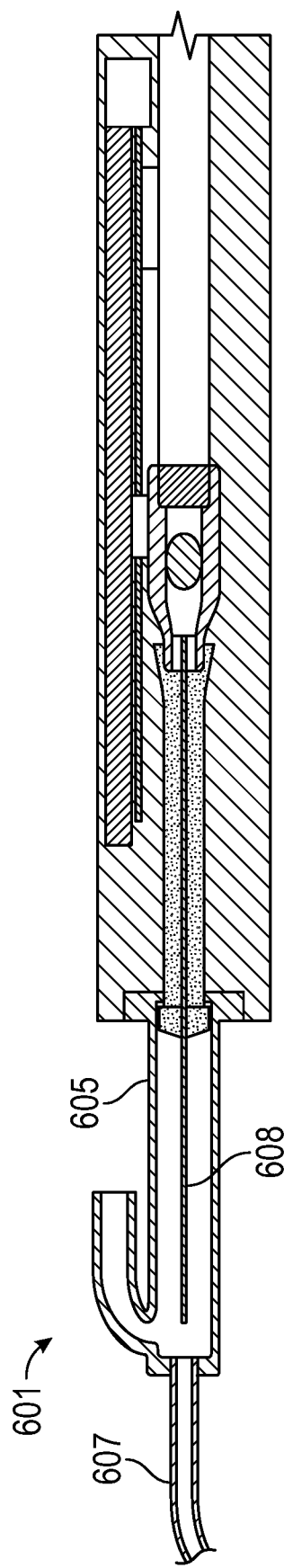
FIG. 7D
FIG. 7E

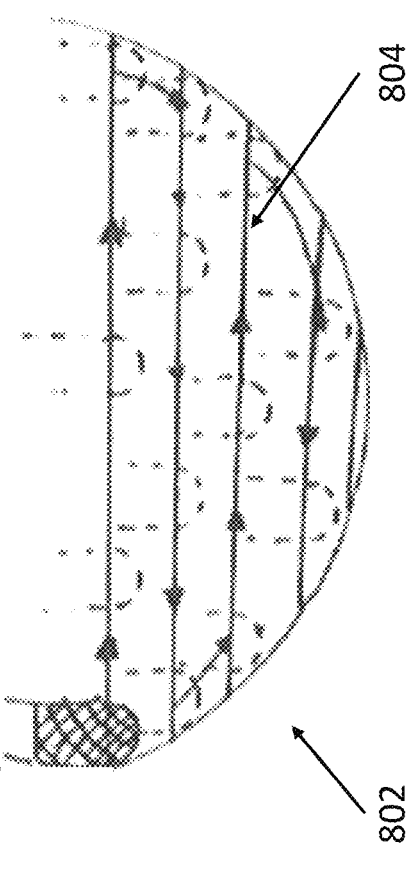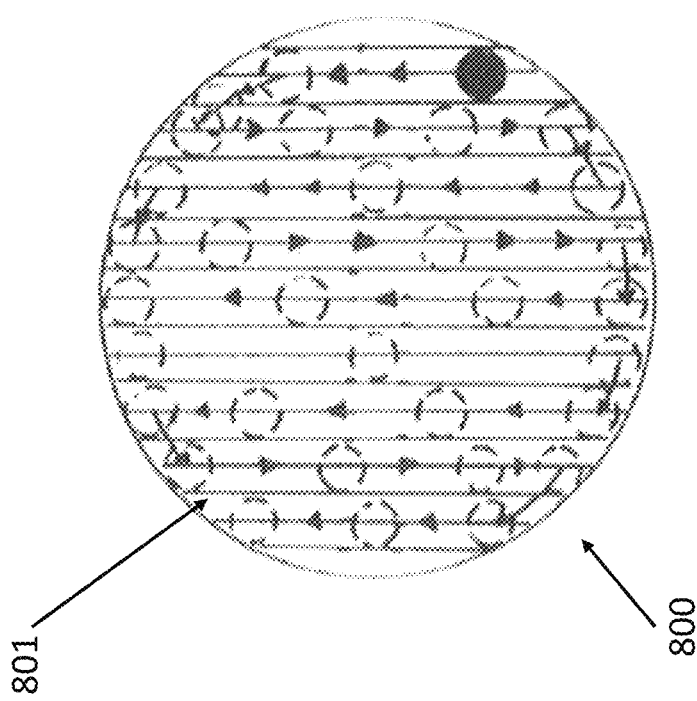

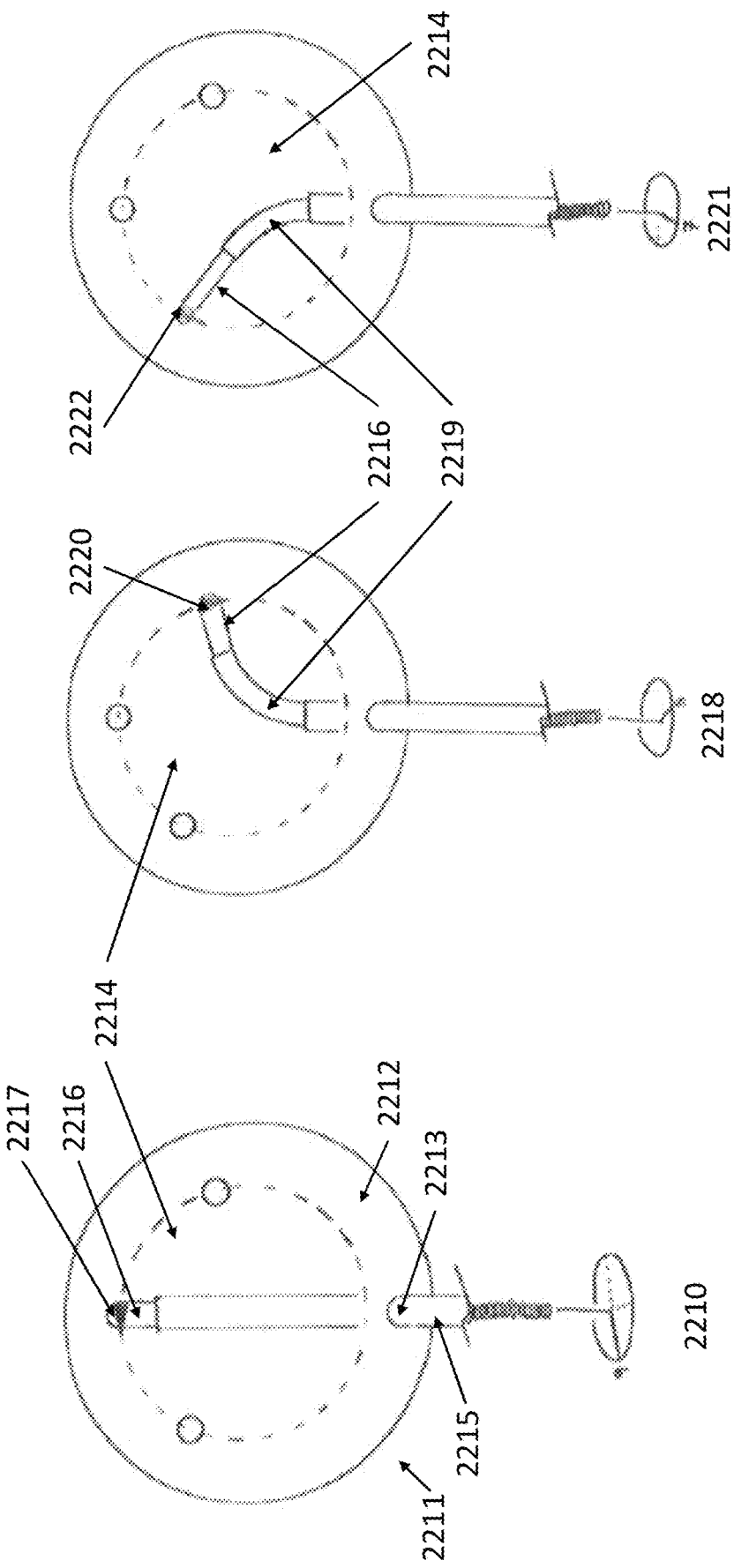

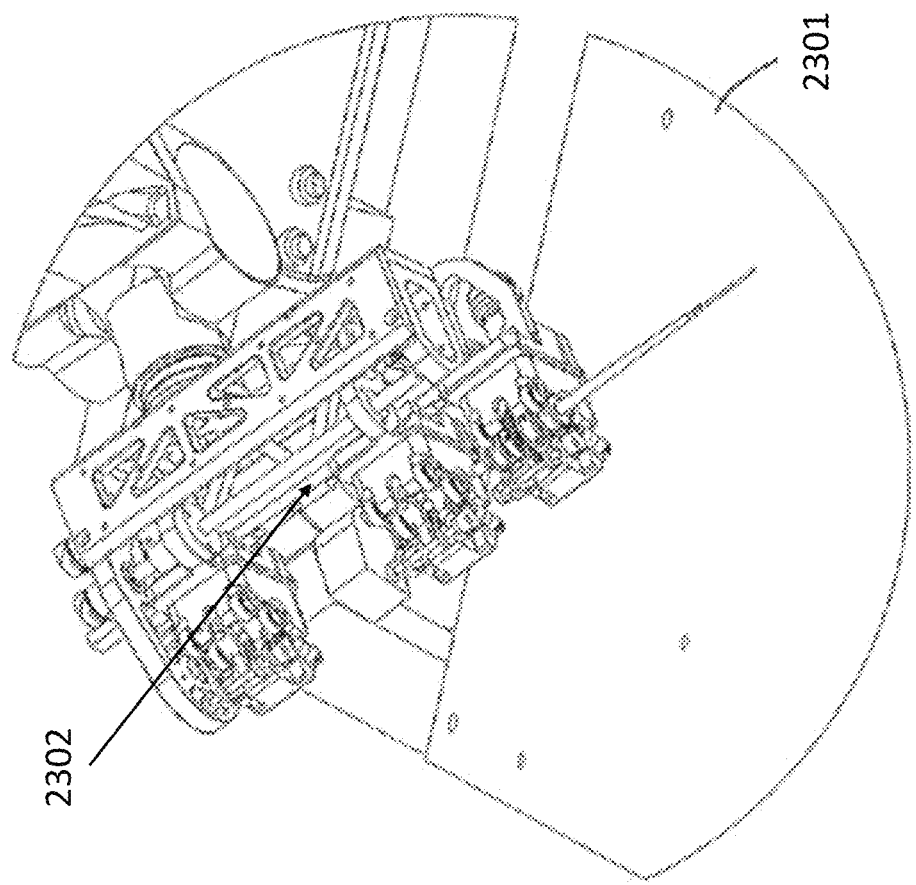
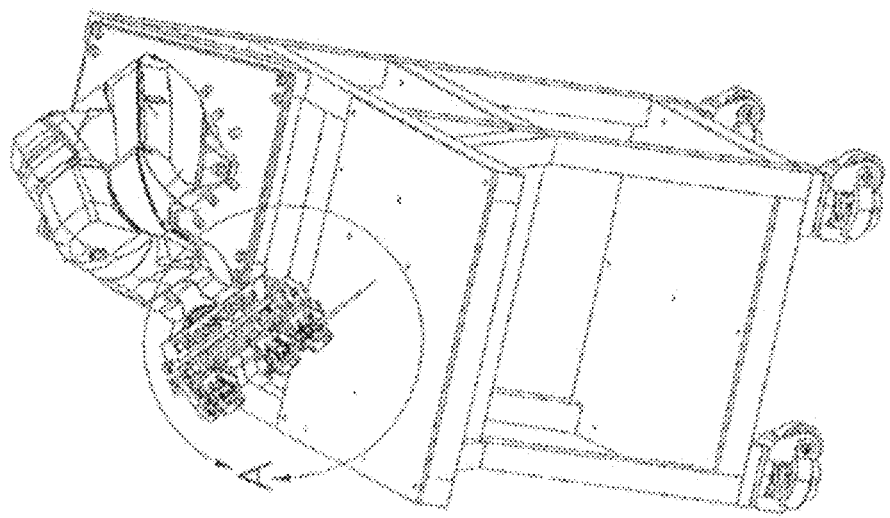
FIG. 23

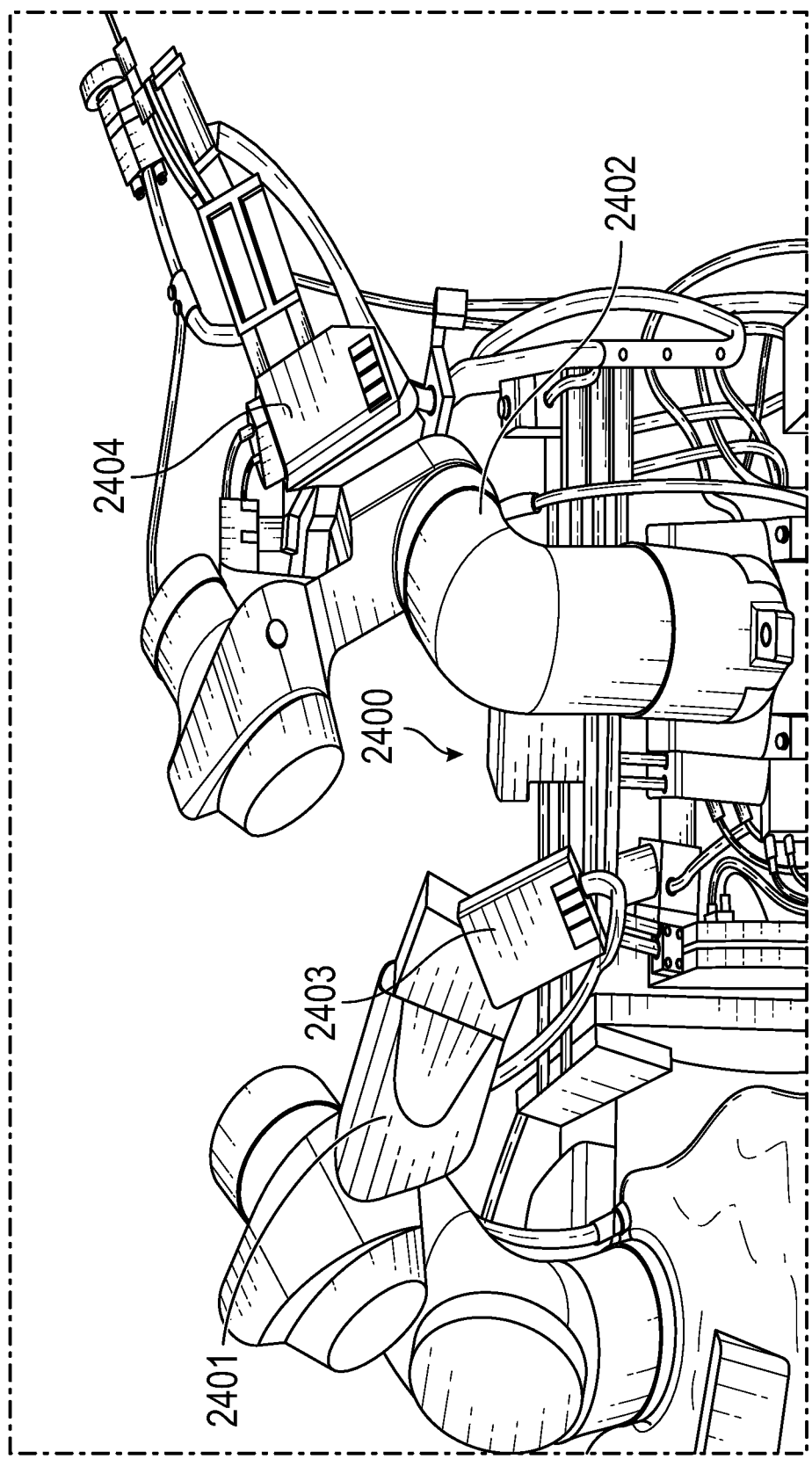

METHODS FOR ROBOTIC ASSISTED CATARACT SURGERY

CROSS-REFERENCE TO RELATED APPLICATIONS

This application claims benefit of U.S. Provisional Application Ser. No. 61/833,835, filed Jun. 11, 2013, the entire content of which is incorporated herein by reference.

BACKGROUND OF THE INVENTION

1. Field of the Invention

The field of the present application generally pertains to medical devices. More particularly, the field of the invention generally pertains to an apparatus, system, and method for robotic assisted cataract surgery.

A "cataract" is a clouding of the lens in the eye that affects vision. Most people develop cataracts due to aging. The condition is not uncommon; it is estimated more than half of all Americans will either have a cataract or have had cataract surgery by age 80.

FIG. 1 is a diagram of the human eye, included for background. The major features of the eye 100 comprise the cornea 101, the anterior chamber 102, the iris 103, the lens capsule 104, the lens 105, the vitreous 106, the retina 107, and the sclera 108. The lens capsule 104 has an anterior surface 109 bordering the anterior chamber 102 and a posterior surface 110 bordering the vitreous 106. Most relevant to cataracts, the lens 105 within the lens capsule 104 is comprised of a nucleus 111 and cortex 112.

As shown in FIG. 1, the lens 105 within the eye 100 lies behind the iris 103. In principle, it works much like a camera lens by focusing light onto the retina 107 at the back of the eye 100 where an image is recorded. The lens 105 also adjusts the focus of the eye 100, allowing it to focus on objects both near and far.

The lens 105 within the eye 100 contains protein that is precisely arranged to keep the lens 105 clear and allow light to pass through it. As the eye 100 ages, the protein in the lens 105 may clump together to form a "cataract". Over time, the cataract may grow larger and obscure a larger portion of the lens 105, making it harder for one to see.

Age-related cataracts affect vision in two ways. The clumps of protein forming the cataract may reduce the sharpness of the image reaching the retina 107. The clouding may become severe enough to cause blurred vision. The lens 105 may also slowly change to a yellowish/brownish tint. As the lens 105 ages, objects that once appeared clear may gradually appear to have a brownish tint. While the amount of tinting may be small at first, increased tinting over time may make it more difficult to read and perform other routine activities.

Surgery is currently the only real treatment for cataracts. Each year, ophthalmologists in the United States perform over three million cataract surgeries. The vast majority of cataracts are removed using a procedure called extracapsular cataract extraction (ECCE). ECCE traditionally comprises of several steps. Incisions must first be made to the cornea 101 in order to introduce surgical instruments into the anterior chamber 102. Through the incisions in the cornea 101 and the space of the anterior chamber 102, the surgeon may remove the anterior face of the lens capsule 109 in order to access the lens underneath 105. This phase of the surgery, known as capsulorhexis, is often the most difficult procedure in ECCE. Having gained access to the lens through capsulorhexis, a small amount of fluid may be injected into the exposed lens capsule 104 to improve access and maneuverability of the lens 105. This phase of the surgery is known as hydrodissection to the skilled artisan.

After loosening the lens, it must be extracted. Traditionally, this phase of the procedure involved manual extraction of the lens through a large (usually 10-12 mm) incision made in the cornea 101 or sclera 108. Modern ECCE is usually performed using a microsurgical technique called phacoemulsification, whereby the cataract is emulsified with an ultrasonic hand piece and then suctioned out of the eye through incisions in the cornea 101.

A phacoemulsification tool may be an ultrasonic hand piece with a titanium or steel needle. The tip of the needle may vibrate at an ultrasonic frequency to sculpt and emulsify the cataract while a pump aspirates particles through the tip. In some circumstances, a second fine steel instrument called a "chopper" may be used to access the cataract from a side port to help with "chopping" the nucleus 111 into smaller pieces. Once broken into numerous pieces, each piece of the cataract is emulsified and aspirated out of the eye 100 with suction.

As the nucleus 111 often contains the hardest portion of the cataract, emulsification of the nucleus 111 makes it easier to aspirate the particles. In contrast, the softer outer material from the lens cortex 112 may be removed using only aspiration. After removing the lens material from the eye 100, an intraocular lens implant (IOL) may be placed into the remaining lens capsule 104 to complete the procedure.

One variation on phacoemulsification is sculpting and emulsifying the lens 105 using lasers rather than ultrasonic energy. In particular, femtosecond laser-based cataract surgery is rapidly emerging as a potential technology that allows for improved cornea incision formation and fragmentation of the cataract.

Phacoemulsification and laser-based emulsification, however, still have their shortcomings. Phacoemulsification requires the use of tools that propagate ultrasound energy along the length of the tool, from a proximal transducer to a distal tip. The propagation leads to the transmission of ultrasound energy along the tool to other tissues proximal to the eye 100. Ultrasound tools also generate more heat than would be desirable for a procedure in the eye 100. In addition, the mechanical requirements of propagating the ultrasound wave along the length of the tool often make it rigid and difficult to steer around corners or bends.

Laser-based tools have their own drawbacks. Presently, manually controlled lasers require careful, precise movement since they can easily generate unwanted heat in the eye 100. Laser fibers in the tool are also fragile, and thus easily damaged when attempting to navigate tight corners. Both limitations increase surgery time and raise safety concerns.

An alternative to conventional laser systems, femtosecond laser systems have their advantages and drawbacks as well. Femtosecond laser systems may be used to create entry sites through the cornea 101 and sclera 108 into the eye 100, as well as to remove the anterior face of the capsule 104. Femtosecond laser energy may be focused within the lens nucleus 111 itself, and used to "pre-chop" the lens nucleus 111 into a number of pieces that can then be easily removed with aspiration. Femtosecond lasers, however, can only fragment the central portion of the lens 105 because the iris 103 blocks the peripheral portion of the lens 105. Thus, use of another emulsification technology—ultrasound or conventional laser—is still necessary to fracture and remove the peripheral portion of the cataract in lens 105, extending total procedure time. Furthermore, femtosecond laser systems are also expensive and costly to operate and maintain.

Therefore, it would be beneficial to have a new method, apparatus, and system for performing all the phases of cataract surgery with improved precision control and reduced procedure time.

SUMMARY OF THE INVENTION

In general, the present invention provides medical methods, apparatus and systems. Exemplary embodiments provide a method, apparatus, and system for robotic assisted cataract surgery. In one aspect, the present invention provides for a system for robotic ophthalmologic surgical procedures comprising an instrument drive mechanism comprising an instrument interface coupled to a robotic tool, wherein the robotic tool comprises a robotic tool tip, and a vision system configured to detect a position of at least one of an anatomical structure of a patient such as an eye of a patient and the robotic tool tip, and generate a signal in response to changes to the position, wherein the instrument drive mechanism is configured to manipulate the robotic tool tip in response to the signal.

In related systems, the system may also comprise a robot master system configured to receive commands from a user and manipulate the robotic tip in response to a change in position of the anatomical structure. In some embodiments, the instrument drive mechanism is a robotic arm. The robotic tool tip will often comprise one or more of a laser device, an ultrasonic device, an irrigation device, and an aspiration device. The instrument interface may be configured to couple to a plurality of different robotic tools such as at least one of a laser device, an ultrasonic device, an irrigation device and an aspiration device. A laser fiber of the laser device may be configured to extend beyond the length of the robotic tool tip. In embodiments with an irrigation device and an aspiration device in the robotic tool tip, the irrigation device and the aspiration device may be jointly configured to maintain a material volume inside an enclosed operative space of the anatomic structure. This may include maintaining a volumetric pressure within the eye of the patient. The vision system may comprises one or more of a white light imaging device, a structured light imaging device, or an optical coherence topographical device. The robotic tool tip may comprise a reflective marker that is configured to be detected by the vision system, or the robotic tool tip may be configured to deploy an umbrella-like structure.

In another aspect, the present invention provides for a method of laser emulsification during cataract surgery comprising detecting a position of at least one of an anatomical structure of a patient such as an eye of a patient and a robotic tool tip using a vision system, generating a signal in response to the position, and manipulating the robotic tool tip using a robotic instrument drive mechanism in response to the signal which may be a change in the position, wherein the robotic tool tip is coupled to a robotic tool that is coupled to an instrument interface of the robotic instrument drive mechanism. The robotic tool may comprise at least one of a laser device, an ultrasound device, an irrigation device, and an aspiration device. A laser fiber of the laser device may be configured to extend beyond the length of the robotic tool tip. The irrigation device and the aspiration device may be jointly configured to maintain a material volume inside an enclosed operative space of the eye of the patient. In related systems, robotically manipulating the robotic tool tip includes robotically maneuvering the robotic tool tip relative to the eye of the patient, robotically changing the pulse repetition rate of the laser device of the robotic tool tip, and robotically changing the pulse energy of the laser device of the robotic tool tip. The instrument drive mechanism may be configured to manipulate the robotic tool in response to a change in the position. The instrument drive mechanism may be configured to manipulate the robotic tool in response to commands from a user.

These and other embodiments are described in further detail in the following description related to the appended drawing figures.

BRIEF DESCRIPTION OF THE DRAWINGS

The invention will be described, by way of example, and with reference to the accompanying diagrammatic drawings, in which:

FIGS. 7A, 7B, 7C, 7D, and 7E are illustrations of tool 601 with retractable laser fiber 608 in various stages of extension and retraction of laser fiber 608;

FIGS. 8A and 8B are illustrations of various views of robotically-assisted lasing paths for laser-based emulsification, according to certain embodiments of the present invention;

FIGS. 22A and FIGS. 22B1-22B3 are illustrations of top-sectional views of robotically controlled capsulorhexis procedures according to certain embodiments of the present invention;

FIG. 23 is an illustration of a robotic apparatus with an instrument drive mechanism to couple tools to a robotic system, according to an embodiment of the present invention; and FIG. 24 is an illustration of a robotic apparatus with a plurality of instrument drive mechanisms and interfaces, according to an embodiment of the present invention.

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. Accordingly, the methods and systems of the present invention are not limited to cataract surgery and other ophthalmologic applications.

Bimanual Approach

The present invention relates to a robotic device to assist surgical procedures in ophthalmology, particularly cataract surgery. In some embodiments, a plurality of robotic devices may be used. In embodiments with two robots, each robot may hold its own laser tool in a dual-tool or "bimanual approach." This approach allows for greater flexibility, as tools may be interchanged, positions may be adjusted, and approaches may be altered to allow for improved access to the operating area. For example, in some embodiments, the robotic arms may move in different patterns to speed up the removal of the cataract. In some embodiments, the robotic arms could move synchronously to treat the same area. Alternatively, both tools could be pointed towards the same general location, while a first tool could be angled from the top down and the other tool angled to undercut the portions of the lens cut by the first tool.

Figure 2:
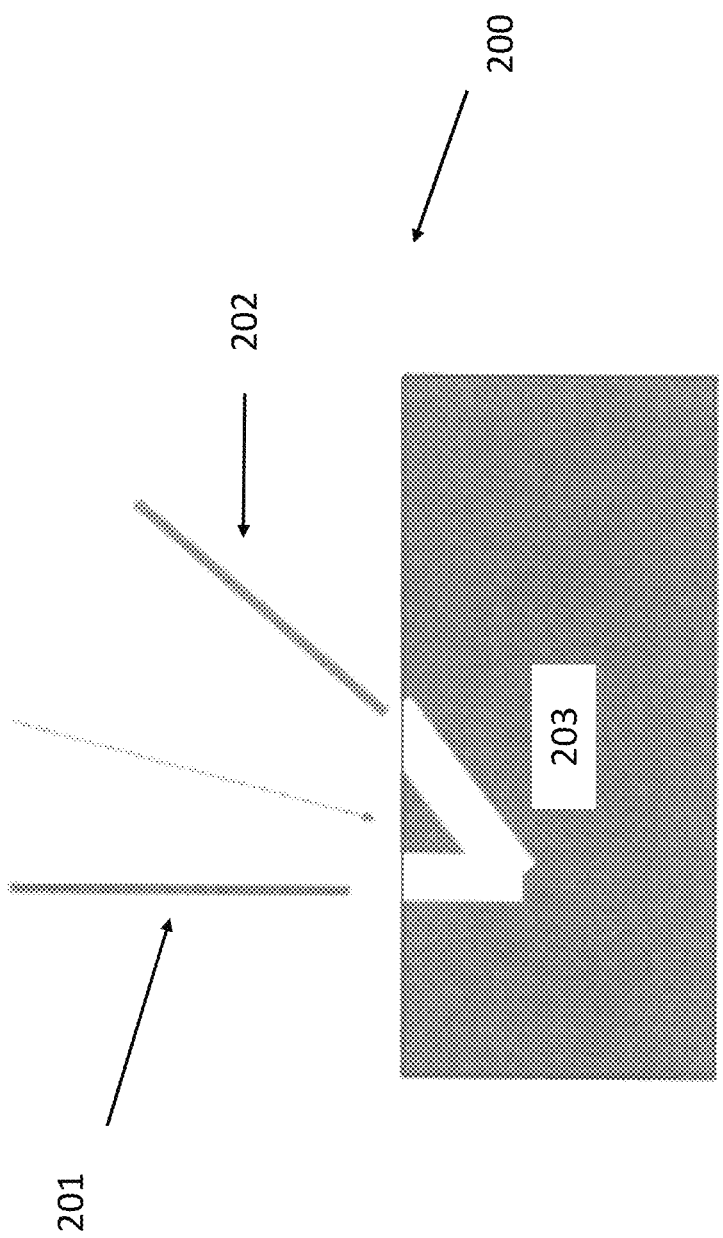
FIG. 2 is an illustration of a robotic surgery system with laser system according to an embodiment of the invention.

FIG. 2 illustrates a robotic surgery system with laser system according to an embodiment of the invention. As shown in FIG. 2, robotic surgery system 200 comprises a first tool 201 and a second tool 202. First tool 201 and second tool 202 may comprise at least one of the following to facilitate removal of cataract material from a sample lens capsule 203: lasers, optical coherence tomography (OCT) sensors, imaging systems, video systems, location sensors, flush devices, aspiration devices, and robotic articulation control.

In one embodiment, tool 201 includes a laser and a device with flush and aspiration capabilities. In one embodiment, tool 201 may be able to break up the cataract with the laser in small precise regions due to the strong absorption of the laser light by the cataract material, or water, mesh, or any thermal or mechanical effect. In some embodiments, the laser light in tool 201 may be altered to "undercut" the larger pieces of cataract material, i.e., use small cuts to remove large pieces.

In some embodiments, a laser in tool 201 may be coupled to the cataract though an optical fiber to a tool in the cataract. In other embodiments, a laser may be coupled through free space optics. In some embodiments, a laser may be emitted at the tip of tool 201. In some embodiments, the pulse energy, repetition rate, and pulse duration of the laser in tool 201 may be controlled in real-time. In controlling these parameters, a user of tool 201 may alter the extent and speed of cataract material removal.

Techniques that incorporate use of a computer-controlled robotic arm with preprogrammed patterns allow for precise control and motion of tool 201 and tool 202. Precise control and constant motion of the tools may allow a user of the tools to optimize the volumetric rate of removal of the cataract material using tool 201 and tool 202.

Figure 3:
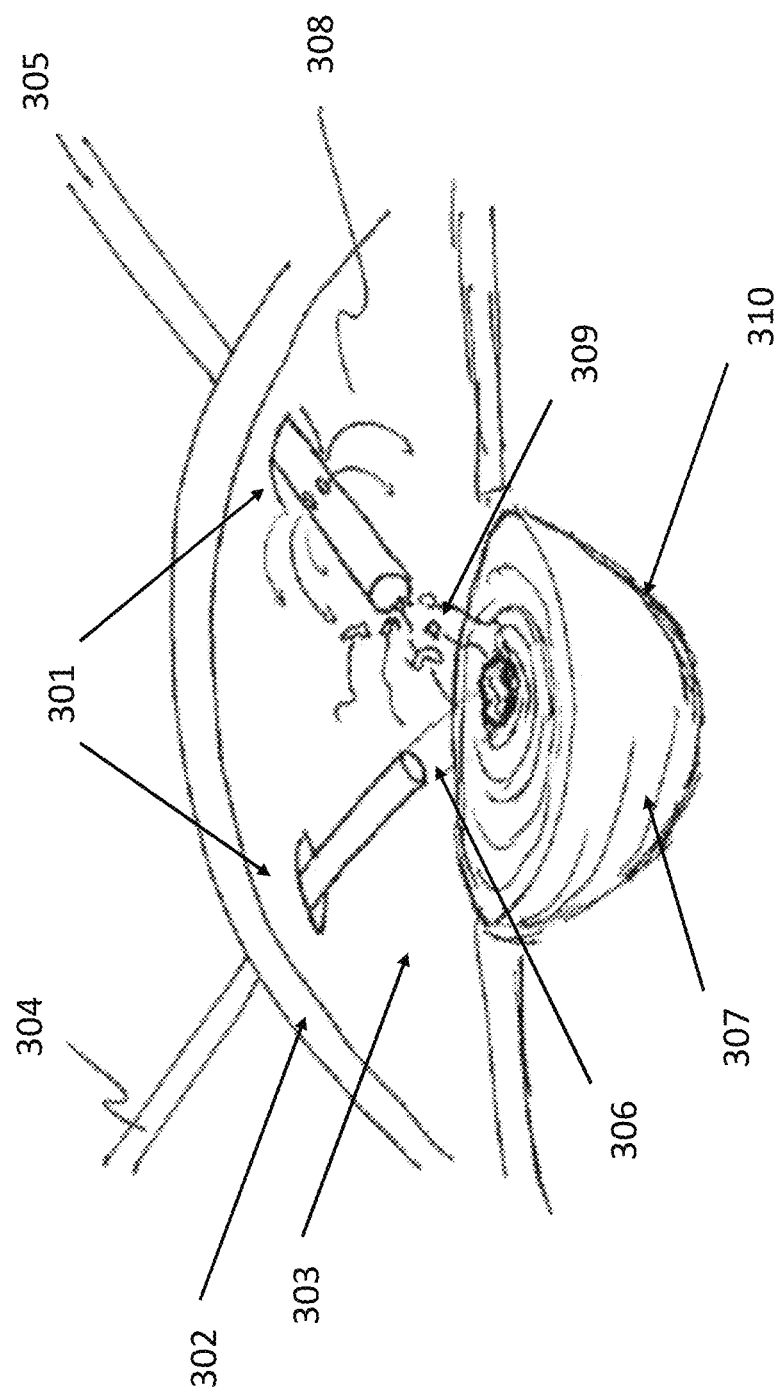
FIG. 3 is an illustration of the use of two tools with separate functionality for laser-based emulsification, irrigation, and aspiration, according to an embodiment of the present invention.

FIG. 3 illustrates an apparatus using two tools for laser-based emulsification in an eye, according to an embodiment of the present invention. In FIG. 3, a first tool 304 and a second tool 305 have separate and distinct functionalities as they operate within the anterior chamber 303 through incisions 301 in the cornea 302 in the eye 300. First tool 304 may emit laser radiation 306 for emulsifying cataract material in the lens 307. Second tool 305 may have flush capabilities 308 and aspiration capabilities 309 to extract the cataract material and maintain the integrity of the anterior chamber 303 and lens capsule 310.

Figure 4:
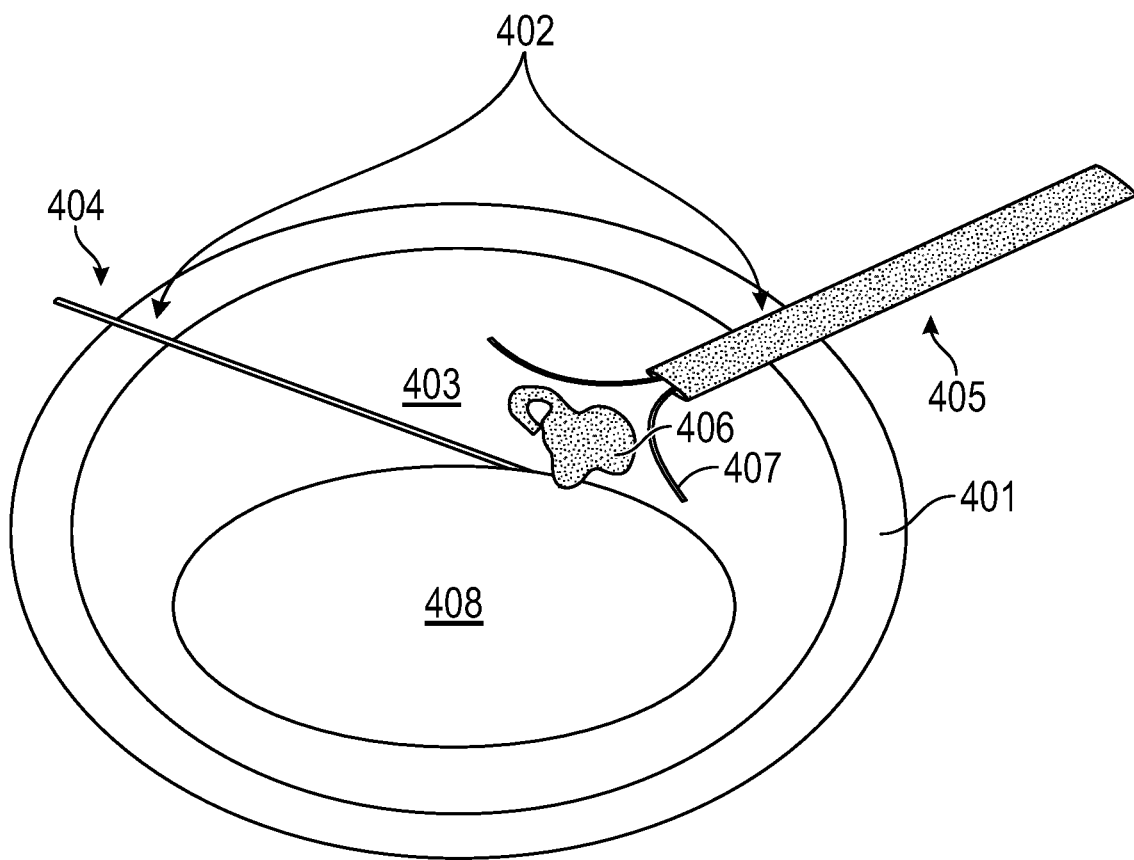
FIG. 4 is an illustration of the use of two tools with separate functionality for laser-based emulsification, according to an embodiment of the present invention.

FIG. 4 illustrates an apparatus using two tools for laser-based emulsification, according to an embodiment of the present invention. In FIG. 4, a first tool 404 with a laser fiber and a second tool 405 with a hollow tube operate in the anterior chamber 403 through incisions 402 in the cornea 401. Laser radiation from first tool 4404 may be used to break up the cataract in the lens 408 during laser-based emulsification. However, the resulting debris plume 406 caused by the breaking up of the cataract could potentially spray and damage the endothelial cells of the lens anterior chamber 403. Accordingly, the hollow tube in second tool 405 may deploy a membrane "umbrella" 407 to shield the endothelial cells of anterior chamber 403 during the emulsification process. Upon completion, umbrella 407 may be retracted back into the hollow tube in second tool 405 through incisions 402 in the cornea 401. In some embodiments, membrane umbrella 407 may be pre-shaped by spines created from nitinol.

Laser Tools

Figure 5:
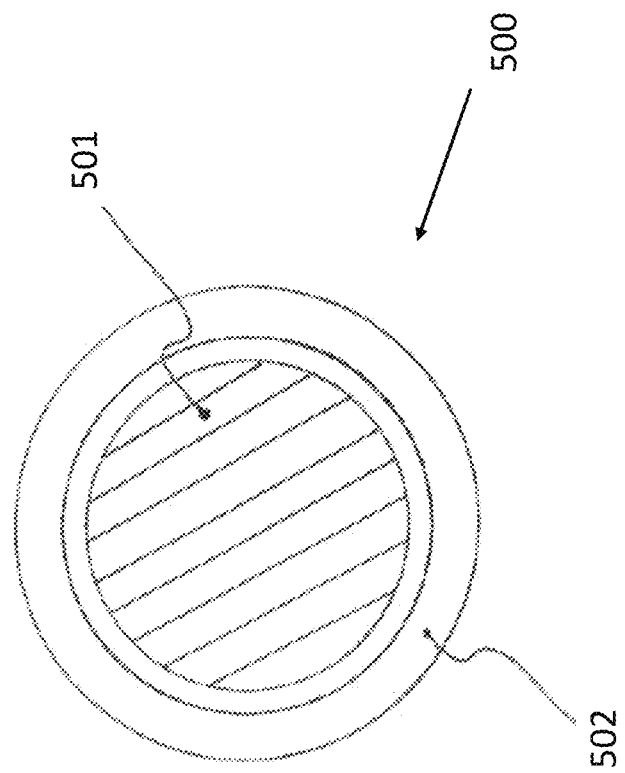
FIG. 5 is an illustration of a cross-sectional view of a simple laser fiber tool for robotic control according to an embodiment of the present invention.

FIG. 5 is a schematic of a simple laser fiber tool for robotic control in accordance with an embodiment of the present invention. As shown in the cross-sectional view of FIG. 5, tool 500 may include a laser fiber 501 and outer tube 502. In some embodiments, the laser signal and energy may be conveyed to the tip of the tool via a photonic waveguide, a set of mirrors, or a set of minors and lenses. In some embodiments, the space between laser fiber 501 and outer tube 502 may be used to conduct flush and aspiration means.

Embodiments of the present invention may incorporate lasers with a wavelength near the water absorption peak at 2 μm, 3 μm, 4.5 μm, 6 μm, or 10 μm. Alternatively, a laser near the protein absorption peak at 280 nm may also be used to remove cataract material.

In some embodiments, tools may also contain more than one laser fiber. This could be used to increase the area that is treated or create lesions that are particular shapes (for example, three fibers in a row could produce a longer more knife-like cut).

During the operation of the laser, the tip of the laser tool may be located some distance away from the anterior portion of the capsule or in contact with the capsule. In the case of the laser tool being in contact with the capsule, the tip of the tool could be shaped to provide maximum cutting effect. Depending on the embodiment, the shapes of the laser tool tip can be flat, round, tapered to a point, or a combination of the flat, round and tapered shapes.

Figure 6A:
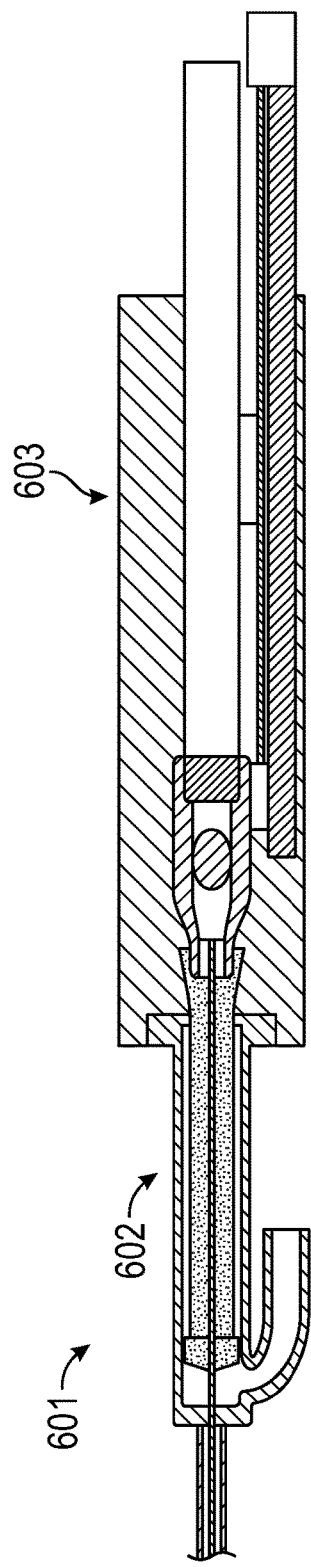
FIGS. 6A, 6B, and 6C are illustrations of a laser fiber suction tube with retractable laser fiber according to an embodiment of the present invention.

FIG. 6 illustrates a laser fiber suction tube with retractable laser fiber in accordance with an embodiment of the present invention. FIG. 6A is a general diagram of tool 601, which contains both a disposable portion 602 and a reusable portion 603.

Figure 6B:
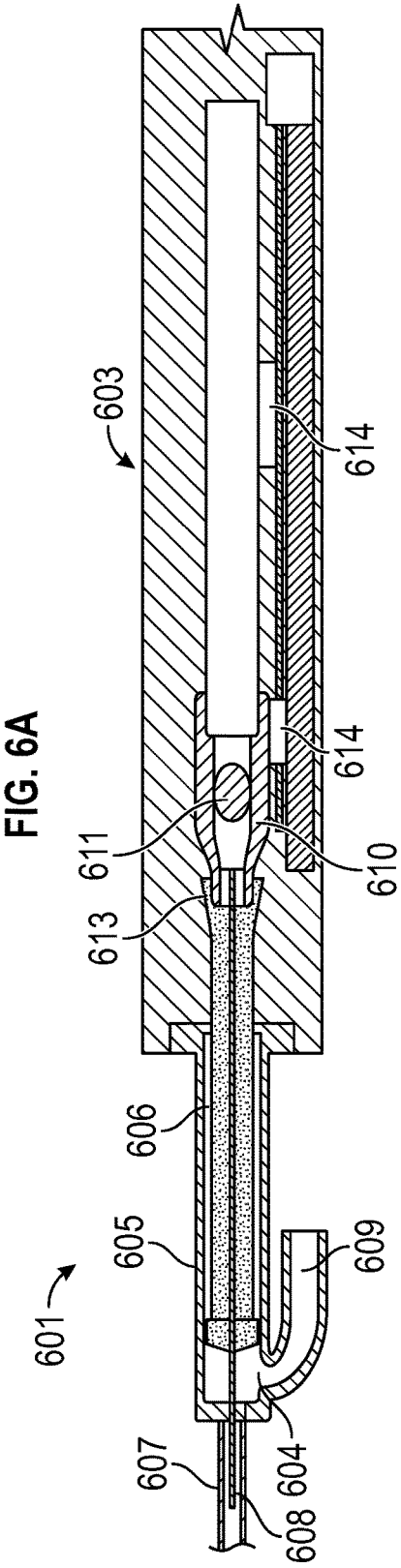

FIG. 6B is a detailed diagram of the components within tool 601 where the plunger 604 is extended into a syringe cylinder 605, which is synonymous with disposable portion 602. Syringe cylinder 605 is proximally connected to reusable portion 603 to allow for the plunger 604 to extend into the plunger support shaft 606. Syringe cylinder 605 is distally connected to a suction tube 607 which may sheath a retractable laser fiber 608. Syringe cylinder 605 may also provide access 609 for aspirational means to suction tube 607. Within reusable portion 603, plunger 604 may be coupled to a lens coupling housing 610, a lens 611 within lens coupling housing 610, and a trunk fiber 612 through a plunger snap fitting 813. Plunger 604 may thus be extended into syringe cylinder 605 or retracted back to reusable portion 603 based on the movement of a controlled slider 614.

Figure 6C:
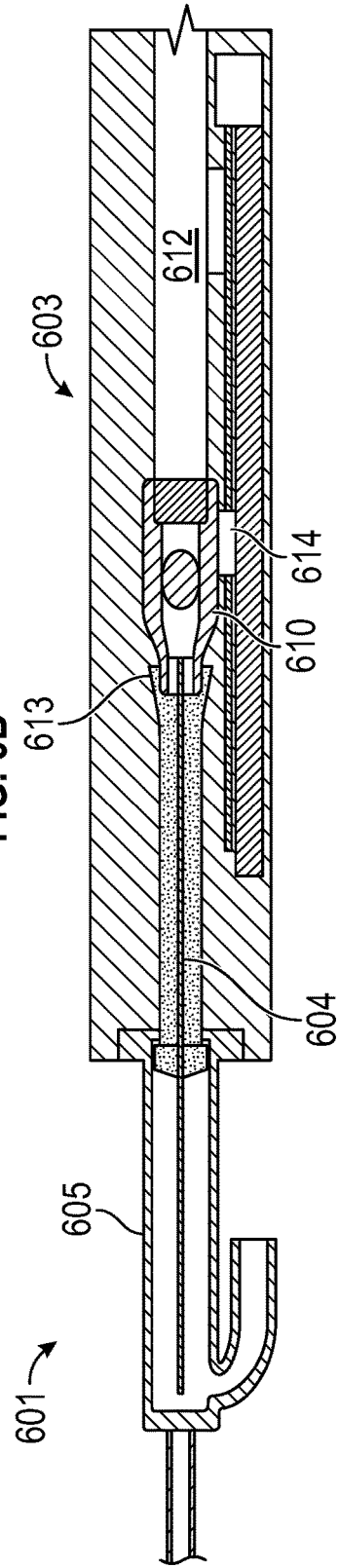

FIG. 6C is a detailed diagram of the components within tool 601 where plunger 604 is recessed into the reusable portion 603. As shown in FIG. 6C, when controlled slider 614 is retracted, trunk fiber 612 and lens coupling housing 610 are also retracted. Accordingly, plunger 604, which is coupled to lens coupling housing 610 through plunger snap fitting 613, is recessed from syringe cylinder 605.

During the emulsification and aspiration of the lens cataract material, the posterior portion of the capsule is at risk of being damaged from the laser radiation and the aspiration force. For example, if portions of the lens capsule membrane are sucked into the aspiration tube, the posterior portion may be stressed and torn. This increases the risk of intrusion of the vitreous fluid into the anterior portion of the eye, which can cause infections and other eye diseases. To minimize that possibility, in some embodiments, the laser fiber can be extended beyond the end of the suction tube to act as a probe when the laser energy is turned off. The use of the laser fiber as a probe prevents the suction tube from approaching the capsular membrane and damaging it. The shape of the laser fiber can be optimized to minimize damage to the membrane. Examples of the shaped tips include rounded or circular tips.

FIG. 7 shows tool 601 with retractable laser fiber 608 in various stages of extension and retraction. In FIG. 7A, the laser fiber 608 is extended beyond the end of the suction tube 607 for purposes discussed earlier. In FIGS. 7B, 7C, 7D, the laser fiber 608 is shown to be retracted such that the end of the laser fiber sits in the suction tube 607. In FIG. 7E, the laser fiber is shown to be retracted such that the end of the laser fiber sits in the syringe cylinder 605. In some embodiments of the present invention, robotic control over preprogrammed patterns of lasing paths may be used to emulsify and aspirate the cataract from the lens capsule. In some embodiments, preprogrammed patterns may control the motion of a tool as well as the laser, flush, and aspiration parameters in order to optimize the removal of lens material. Compared to a manual technique, use of a computer-controlled robotic arm with preprogrammed patterns allows more precise control over the tool tip, generating more accurate patterns and more consistent motion that optimize the volumetric rate of removal during emulsification.

FIG. 8 illustrates different views of robotically-assisted lasing paths for emulsification, according to some embodiments of the present invention. FIG. 8A shows a lasing path 801 with parallel paths in the lens material 800 from the perspective of the anterior chamber and anterior portion of the lens capsule. Using a side-perspective, FIG. 8B shows the depth of a parallel lasing path 804 of the tool tip 803 in the lens material 802. In some embodiments, the emulsification process is at least partially enabled by a cavitation bubble that is created from steam generated by laser energy from a laser tool and fluid from an irrigation tool. The resulting shockwave from a steam-based cavitation bubble results in a larger laser effective zone. In some embodiments, the cavitation bubble may be based on different thermal, mechanical, and shock waves.

Figure 9B:
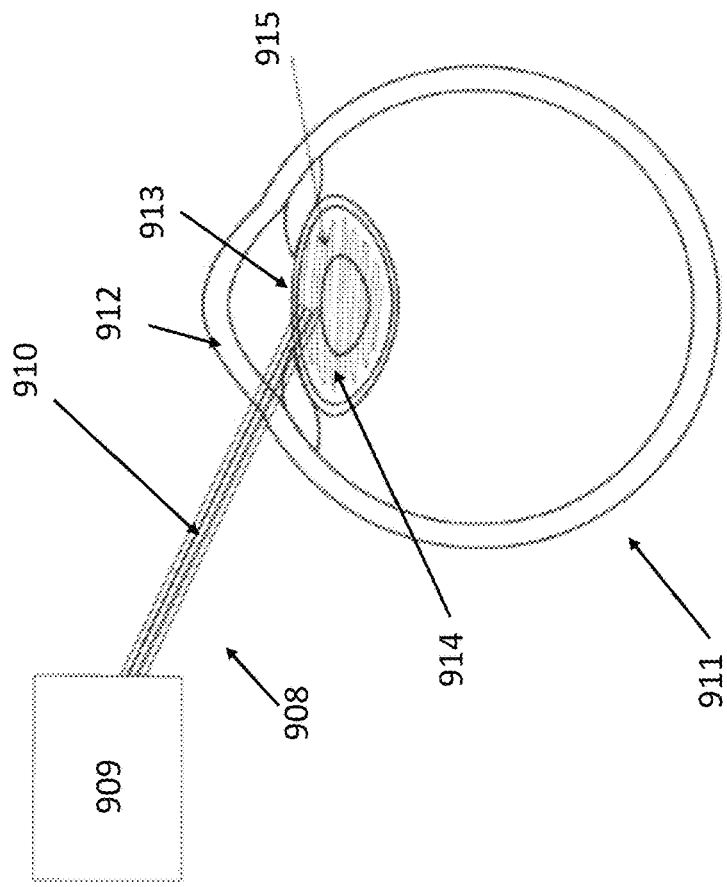
FIGS. 9A and 9B are illustrations of robotic laser tools that execute a preprogrammed lasing pattern for laser-based emulsification and aspiration, according to certain embodiments of the present invention.
Figure 9A:
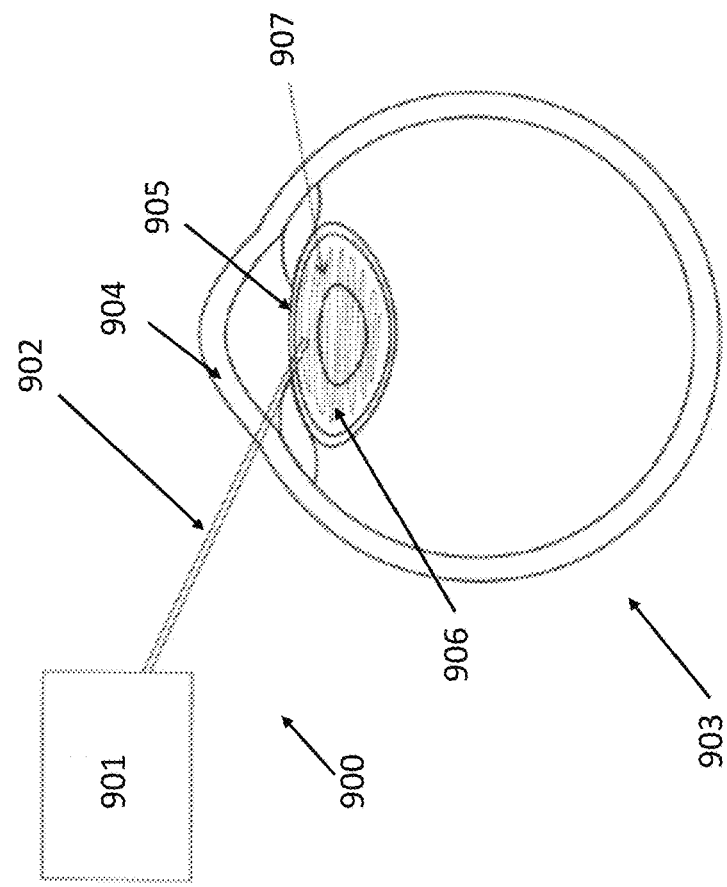

FIG. 9 illustrates an embodiment of the present invention where a preprogrammed emulsifying lasing pattern may be executed either with a simple laser tool (FIG. 9A), or a laser tool with integrated flush and aspiration means (FIG. 9B). FIG. 9A shows an apparatus 900 comprising a robot arm 901 and laser-based tool tip 902 as it follows a preprogrammed lasing pattern 907 inside the lens 906 through incisions in the cornea 904 and the lens capsule 905 of an eye 903. FIG. 9B shows an apparatus 908 comprising a robot arm 909 and tool tip 910 with laser and integrated flush and aspiration capabilities as it follows a preprogrammed lasing pattern 915 inside the lens 914 through incisions in the cornea 912 and the lens capsule 913 of an eye 911.

Figure 10:
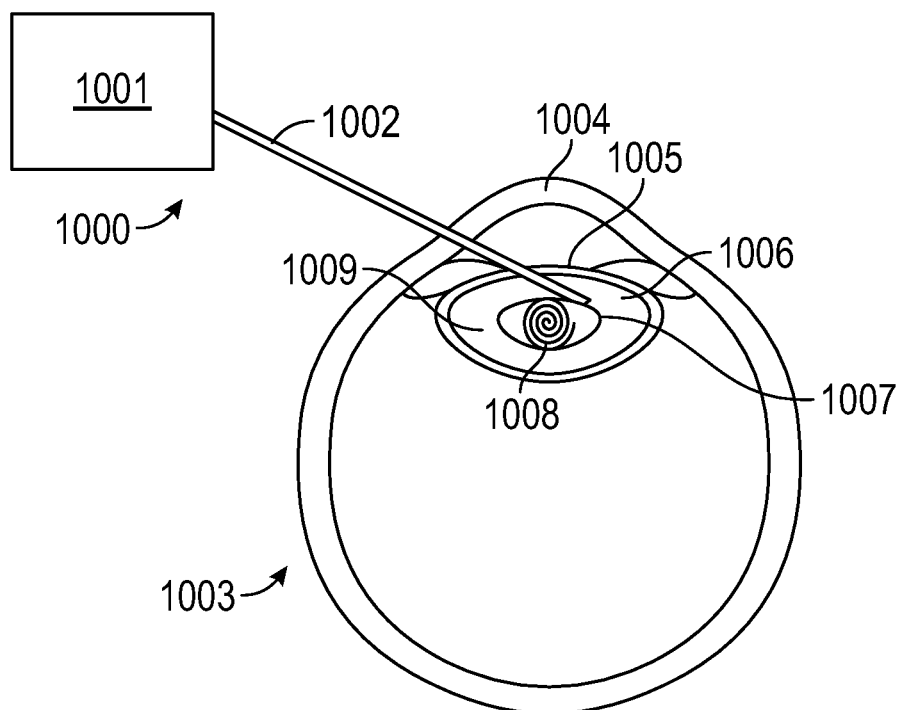
FIG. 10 is an illustration of a robotic laser tool that executes a preprogrammed spiral lasing pattern for laser-based emulsification, according to an embodiment of the present invention.

FIG. 10 illustrates an embodiment of the present invention executing a preprogrammed emulsifying lasing pattern that starts in the center of the eye and spirals out, effectively taking the nucleus of the eye out while leaving the cortex in place. The spiral lasing pattern may be executed by an apparatus 1000 with a robot arm 1001 controlling a laser tool 1002 that follows a spiral tool path 1007 through lens material 1006 within a lens capsule 1005 in eye 1003. Spiral tool path 1003 starts in the center of lens capsule 1005 to affect the nucleus 1008 and terminates to avoid the cortex 1009. The spiral lasing pattern affords more precise targeting of the hard cataract in the nucleus 1008 while also avoiding the cortex 1009 in order to minimize the potential damage to delicate membranes associated with the lens capsule 1005.

FIG. 11 provides several diagrams and charts to illustrate a laser-based emulsification protocol that manipulates the pulse energy, tool tip speed, and pulse repetition rate based on the progress of the tool along a predetermined tool path in accordance with an embodiment of the present invention. FIG. 11A illustrates an embodiment of the present invention where the emulsification tool tip 1101 travels along a simple tool path 1102 within a lens capsule 1103.

Figure 11A:
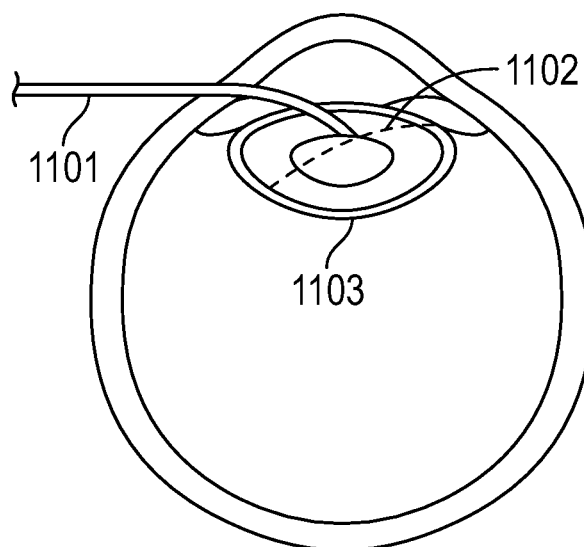
FIGS. 11A, 11B, 11C, and 11D are illustrations and diagrams that show a lasing protocol that manipulates the pulse energy, tool tip speed, and pulse repetition rate based on the progress of the tool along a predetermined tool path according to an embodiment of the present invention.
Figure 11B:
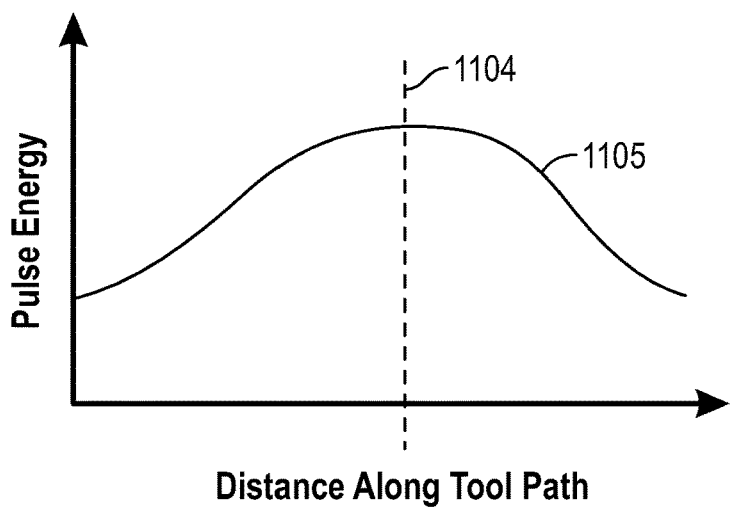

FIG. 11B provides a chart detailing how the laser pulse energy varies depending on the tool tip distance along the tool path. As shown by line 1105, the preprogrammed protocol increases the laser pulse energy during the midpoint of the tool path, represented by a vertical dotted line 1104, where the laser is aimed at the nucleus, where the cataract is often hardest.

Figure 11C:
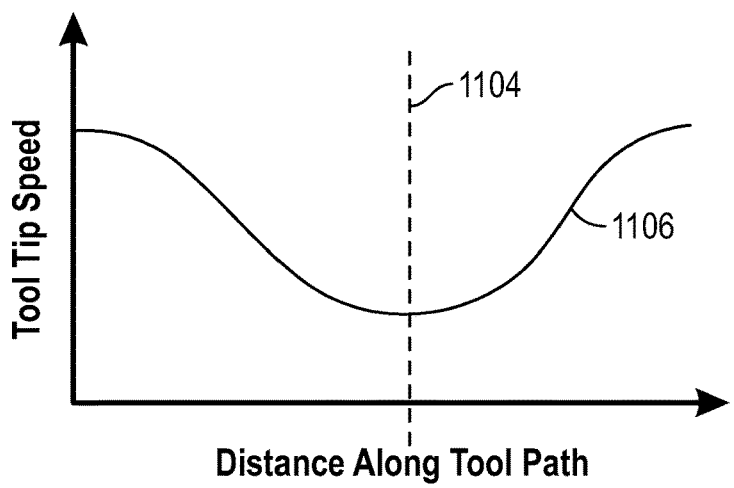

FIG. 11C provides a chart detailing how the tool tip speed varies depending on the tool tip distance along the tool path. As shown by line 1106, the preprogrammed protocol slows tool tip speed during the mid-point 1104 of the tool path where the laser is aimed at the nucleus, where the cataract is often hardest.

Figure 11D:
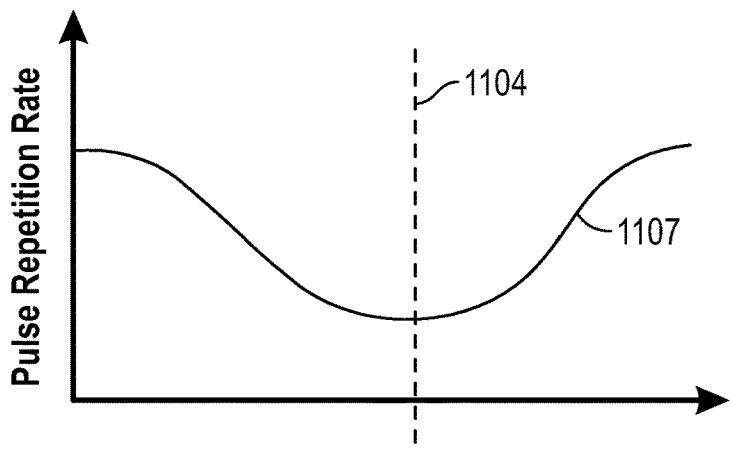

FIG. 11D provides a chart detailing how the pulse repetition rate varies depending on the tool tip distance along the tool path. As shown by line 1107, the preprogrammed protocol slows pulse repetition rate during the mid-point 1104 of the tool path where the laser is aimed at the nucleus, where the cataract is often hardest. In contrast, the pulse repetition rate may be increased at the beginning and end of the tool path, when the tool tip is directed to the cortex, thereby compensating for the speed and/or improved removal of the softer lens cortex materials.

In some embodiments, lower pulse repetition rate leads to greater laser pulse energy. In some embodiments, the spacing between the arms of the spiral may be varied depending on the size of debris to be removed by aspiration. For example, if larger pieces can be removed, the arms of the gaps between neighboring paths of the spiral may become wider. As less cutting is required to break up the cataract, expanding the distance between the arms of the spirals helps reduce the cutting time. This protocol likely necessitates robotic control because due to precise spacing within the lens capsule makes the protocol very difficult to accomplish with a purely manual technique.

In some embodiments, raster patterns may remove material in a systematic x-y-z, grid-like motion. In other embodiments, a radial pattern reminiscent of a typical quadrant chop-and-divide technique may be employed.

In some embodiments, an emulsification patterns may remove lens material from the anterior portion of the cortex, remove by lens material from the center of the nucleus, before removing the remainder of the lens material in other portions of the cortex.

Flush and Aspiration Tools

In yet another embodiment, the robotic system includes real-time control of a flush and aspiration device to remove debris from the chamber. Robotically-controlled fluidic flush and aspiration tool may improve the precision and accuracy of the procedure to maintain the material volume in an enclosed operative space like the interior of an eye. In some embodiments, a tool with a laser device may also have flush and aspiration capabilities. In the alternative, a second tool may include a dedicated aspiration and flush tool.

Figure 12:
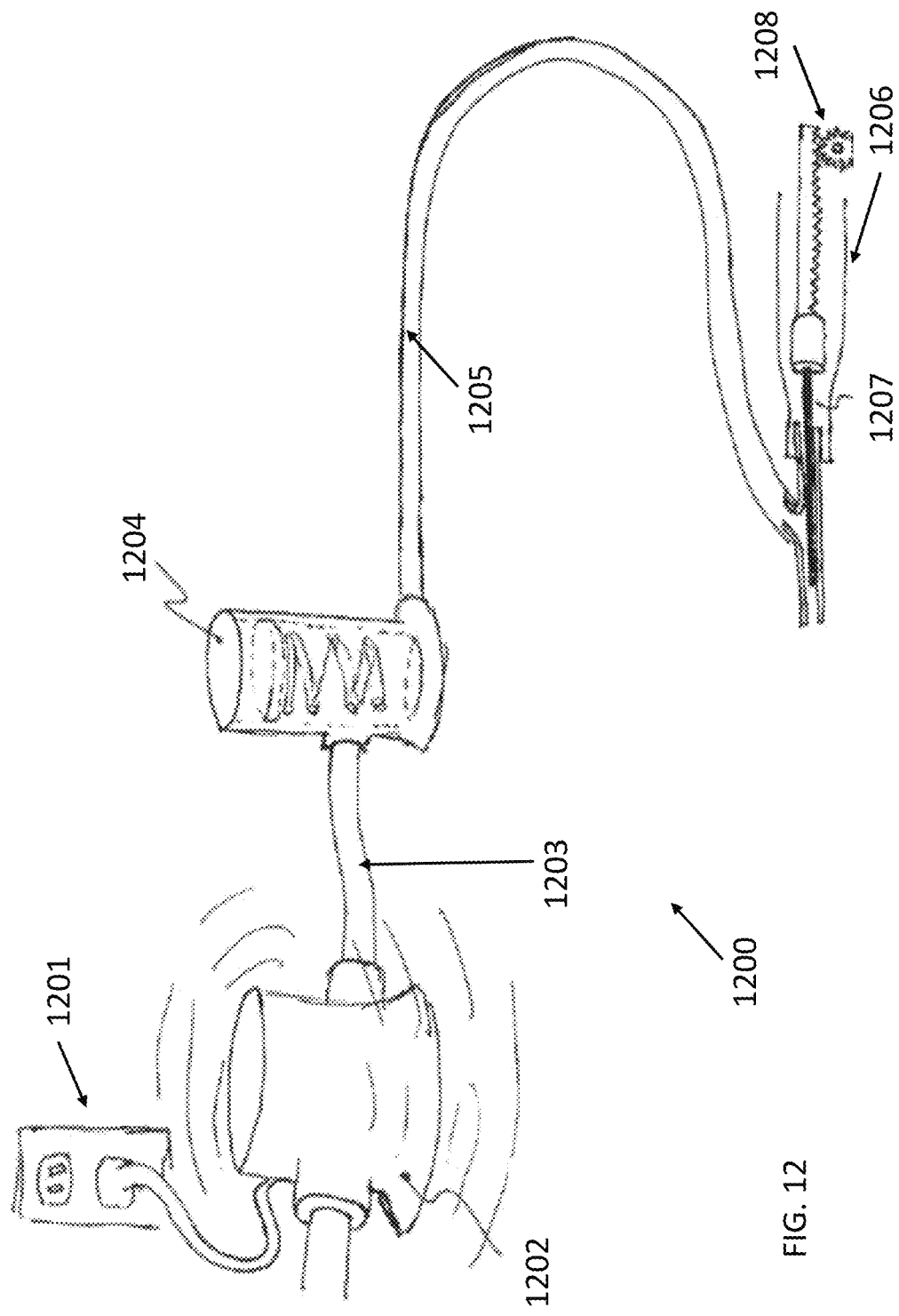
FIG. 12 is a structural illustration of an apparatus with a laser fiber and a means of aspiration, according to an embodiment of the present invention.

FIG. 12 illustrates structural components of an apparatus with a laser fiber and a means of aspiration, in accordance with an embodiment of the present invention. As shown in FIG. 12, apparatus 1200 comprises a power source 1201 that provides electricity to a vacuum pump 1202 coupled through a hose 1203 to a dampener 1204. The aspiration flow may be transferred from the dampener 1204 to a tool 1206 through a tube 1205. The dampener 1204 (represented by a plunger within a cylinder) moderates spikes and dips in the aspiration pressure in cases of air blockage or occlusion in tool 1206.

In addition to aspiration means, the tool may also comprise a laser fiber 1207 that may be extended or retracted using various mechanical means, such with axial motion from a gear 1208. In this particular embodiment, all aspirated cataract material passes near the laser fiber in the aspiration tube as it is being evacuated from the eye.

The size of the flush and aspiration channels also directly influence the size of the pieces of cataract that can be extracted from the lens capsule. Hence, the size of the channels could influence the emulsification patterns of the robotic procedure.

FIG. 13 illustrates block diagrams of several embodiments of the present invention with real-time flush and aspiration control. FIG. 13A illustrates a block diagram of apparatus 1300 with real-time flush control, in accordance with an embodiment of the present invention. In FIG. 13A, apparatus 1300 incorporates a pump 1302 controlled by a computer 1308, a pressure vessel 1304, and a flow rate meter 1306. In apparatus 1300, fluid 1301 is supplied to pump 1302. Pump 1302 directionally forwards the fluid to pressure vessel 1304 via a tube 1303. The fluid pumped into pressure vessel 1304 forces liquid that was originally resting in pressure vessel 1304 toward the flow rate meter 1306. The flow rate meter detects the velocity of the liquid 1305 prior to output 1310 from apparatus 1300. Information regarding the velocity of liquid flow is sent to computer 1308, which can send pressure signal 1309 to pump 1302. This creates a feedback loop; by communicating a flow rate feedback signal 1307 to computer 1308, computer 1308 can respond to the velocity of the exiting liquid 1305 by controlling the pump 1302 through pressure signal 1309. Hence, if the flow of liquid 1305 is too great, the flow of fluid from the pump 1302 through tube 1303 may be adjusted downward. Alternatively, if the flow of liquid 1305 is too low, the flow of fluid from pump 1302 through tube 1303 may be increased to exert more pressure on the liquid in pressure vessel 1304. The increased pressure in pressure vessel 1304 results in increased flow of liquid 1305. This feedback loop enables apparatus 1300 to moderate its liquid flow to a desired flush rate at output 1310.

Figure 13A:
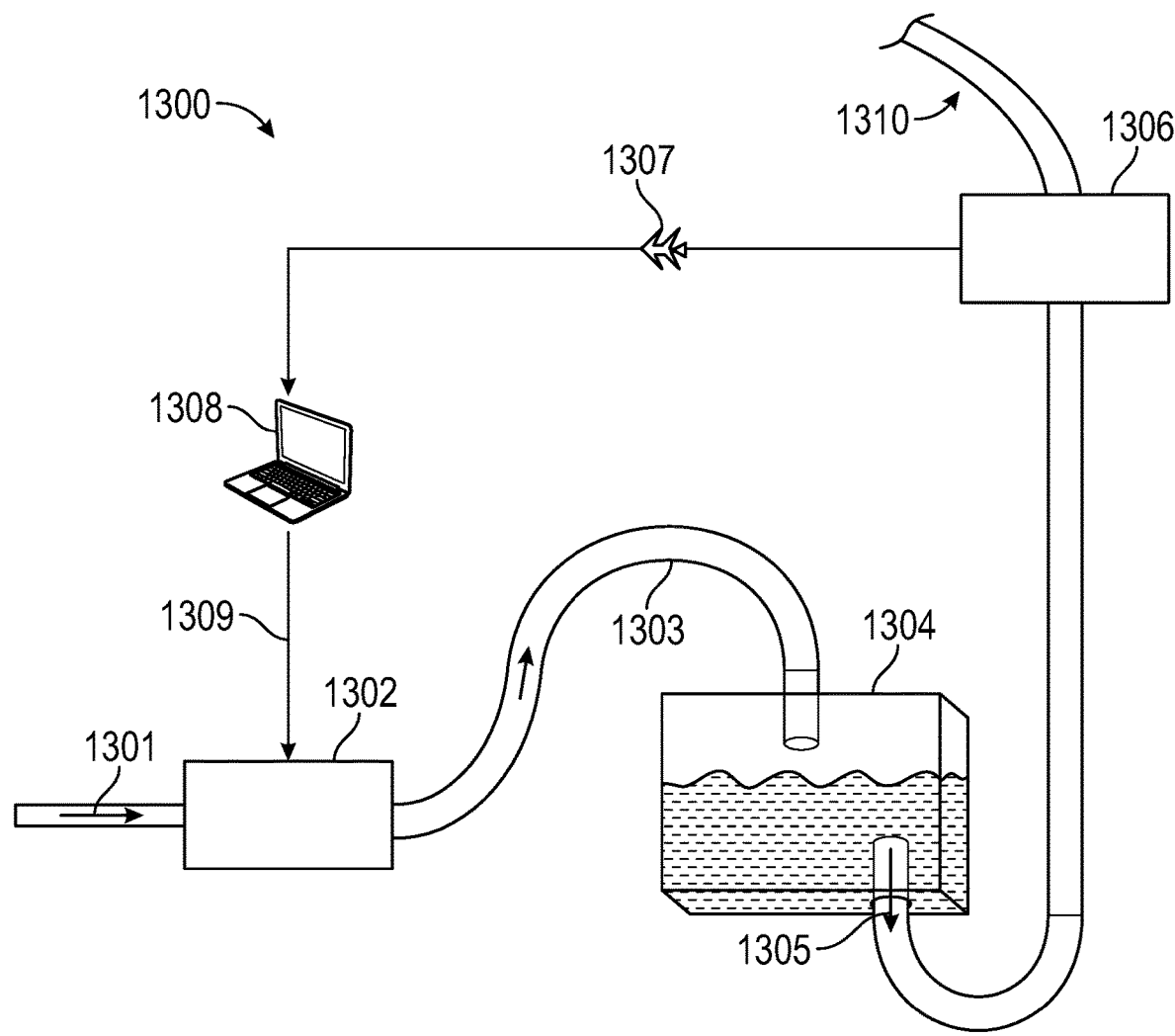
FIGS. 13A, 13B, 13C, and 13D are block diagrams of systems with real time flush and/or aspiration control, according to certain embodiments of the present invention.
Figure 13B:
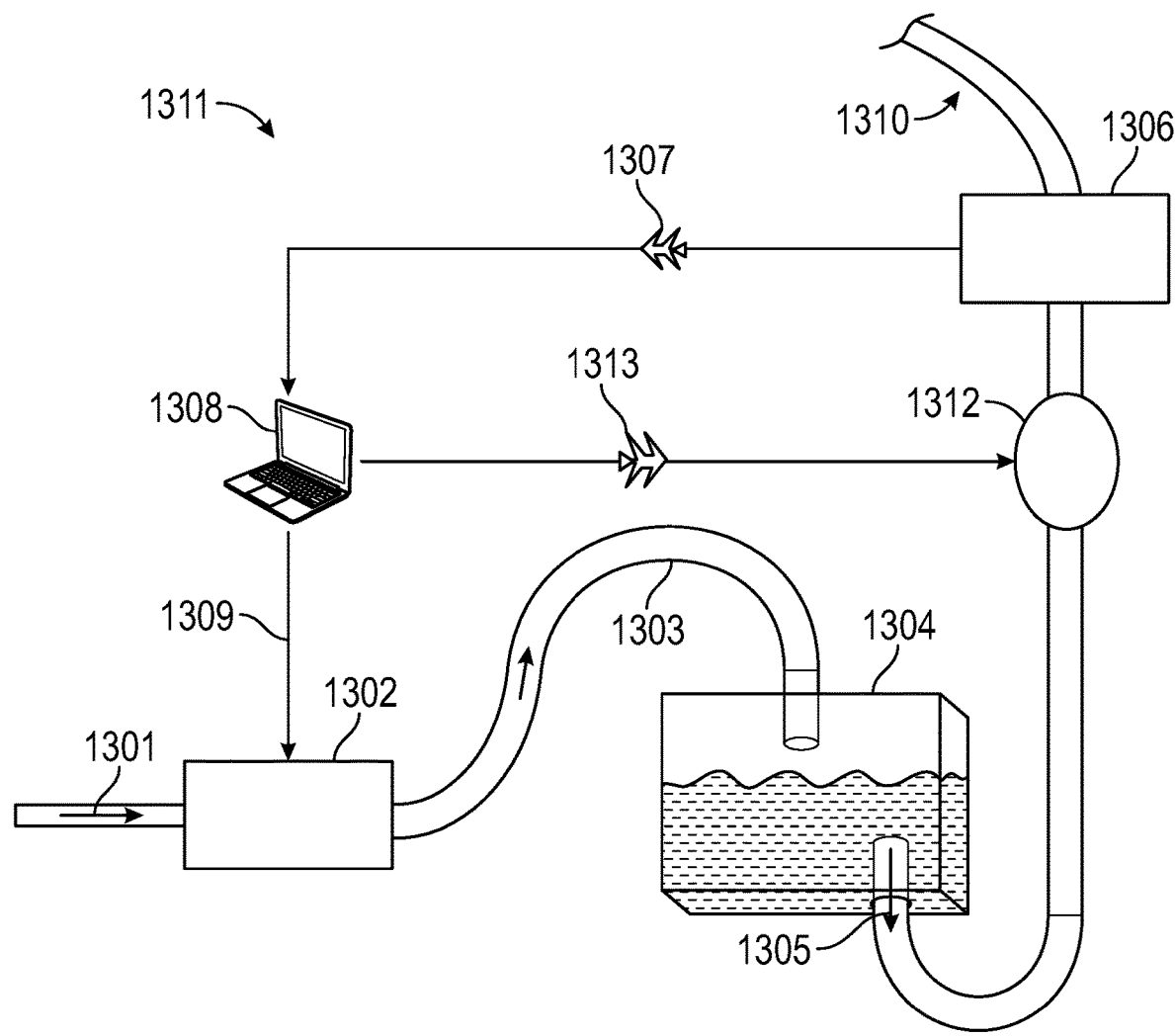

FIG. 13B illustrates a block diagram of apparatus 1300 from FIG. 13A with the addition of a throttle valve to help facilitate the flow rate, in accordance with an embodiment of the present invention. In this embodiment, represented as apparatus 1311, a throttle valve 1312 receives the flow control signal 1313 from either a computer, central processing unit, microcontroller, ASIC, or other control circuitry which is represented as 1308. The throttle valve 1312 may further affect fluid flow by limiting ("throttling") the fluid output from apparatus 1311.

Figure 13C:
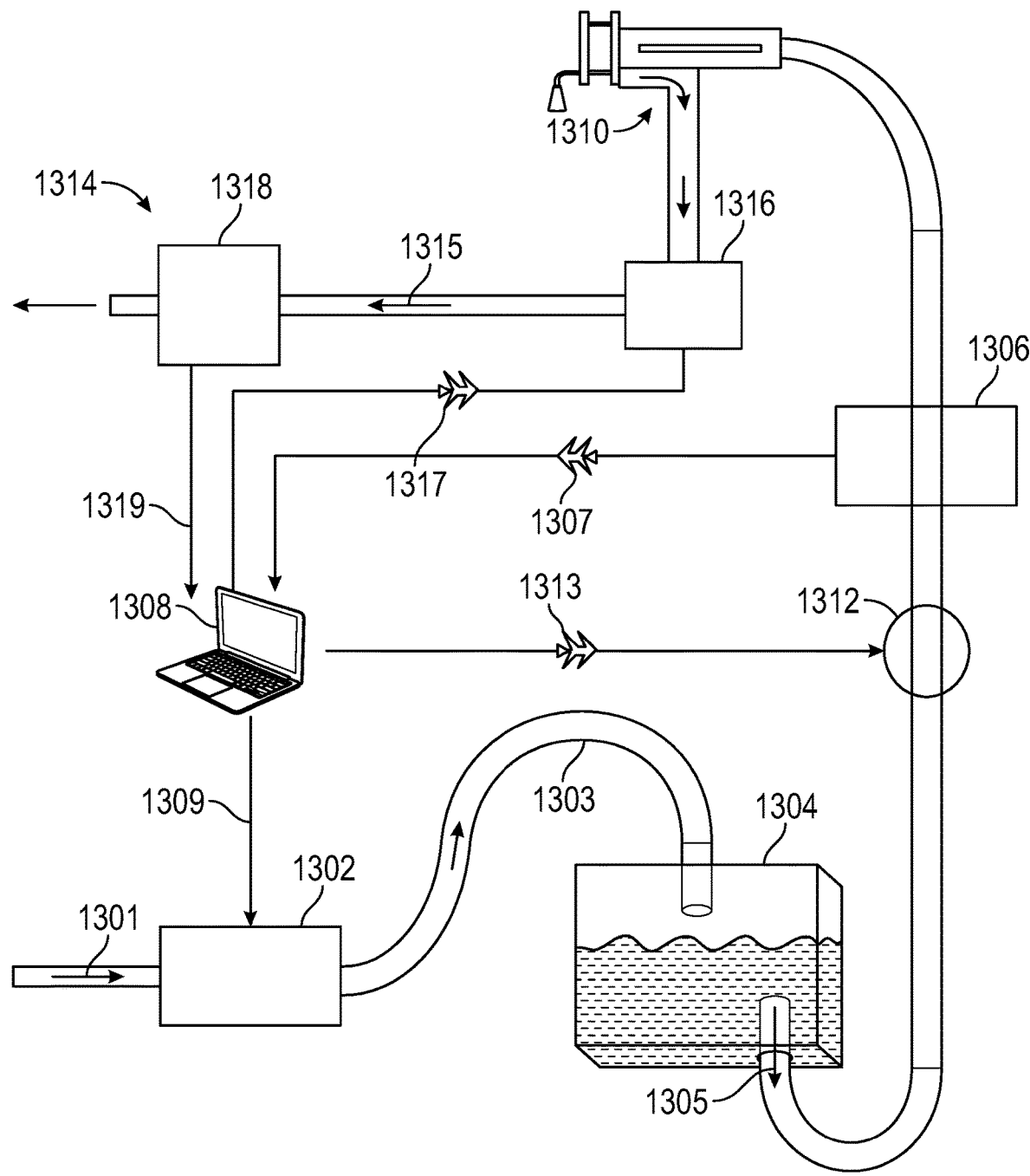

FIG. 13C illustrates a block diagram of apparatus 1311 from FIG. 13B combined with an aspiration pump that removes material from the operative site, in accordance with an embodiment of the present invention. In this embodiment, represented by apparatus 1314, a desired aspiration flow 1315 may be obtained by controlling the aspiration pump 1316 with an aspiration control signal 1317 from computer 1308, which may also be a central processing unit, microcontroller, ASIC, or other control circuitry. In some embodiments, computer 1308 may control the pump 1302, the throttle valve 1312, and the aspiration pump 1316, using the pressure signal 1309, flow (flush) control signal 1313, and the aspiration control signal 1317 respectively. In some embodiments, the aspiration control signal 1317 may be generated by the computer 1308 in response to the aspiration flow rate feedback signal 1319 received from the aspiration flow rate meter 1318 and the flow rate feedback signal 1307 from tool flow rate meter 1306.

Thus, the tool flow rate meter 1306 and aspiration flow rate meter 1318 may be monitored to track the irrigation and aspiration flows in order to maintain an appropriate volume in an enclosed operative space like the interior of an eye of a patient. In this configuration, irrigation and aspiration flow may be moderated or interrupted in real-time using pump 1302, throttle valve 1312, and/or aspiration pump 1316. This may be done in the event that the aspiration path is unable to match the desired flow rate due to blockage, pinched tube, or other mechanical failure.

In some embodiments, the pressure signal 1309 may send a signal indicating fixed pressure to pump 1302. In those embodiments, irrigation (flush) flow may be maintained using flow (flush) control signal 1313 to control throttle valve 1312.

Figure 13D:
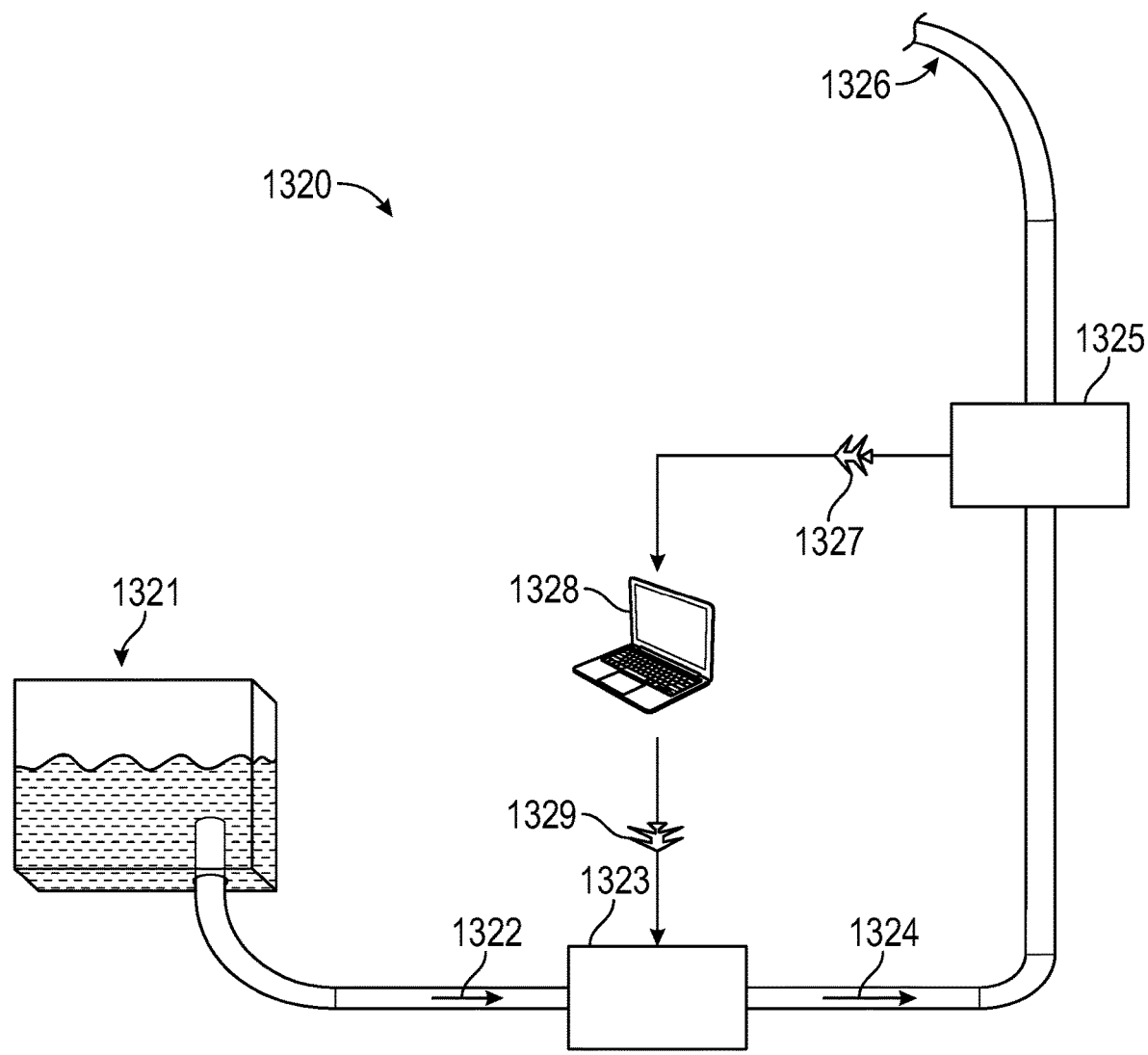

FIG. 13D illustrates a block diagram of an apparatus with real-time flush control where the fluid originates from a fluid reservoir, in accordance with an embodiment of the present invention. In FIG. 13D, fluid 1322 in apparatus 1320 originates from fluid reservoir 1321. Fluid 1322 enters pump 1323 and the pumped output fluid 1324 sent to flow rate meter 1325 prior to output 1326. Similar to the flow rate meter 1306 from FIGS. 13A, 13B, and 13C, the flow rate meter 1325 communicates a feedback signal 1327 about the readings from the flow rate meter 1325 to a computer, central processing unit, microcontroller, ASIC, or other control circuitry (represented as 1328) that controls the pump 1323 using a pump control signal 1329. Unlike in FIGS. 18A, 18B, and 18C, the irrigation flow at output 1326 is directly-controlled by the control signal 1329 to pump 1323, rather than indirectly through a pressure vessel.

Sensor & Imaging Tools

In one embodiment, a locational sensor or imaging technique may also be used to localize different portions of the cataract and the size of the cataract. Such locational sensors or imaging techniques may include 3D imaging, OCT, MRI, CT, Ultrasound, Intra-operative (OCT) or video systems with processing. In some embodiments, the tool itself may have an OCT device. In some embodiments, the tool may have multiple degree of freedom (dof) sensors, such as electromagnetic or fiber sensors.

Figure 14:
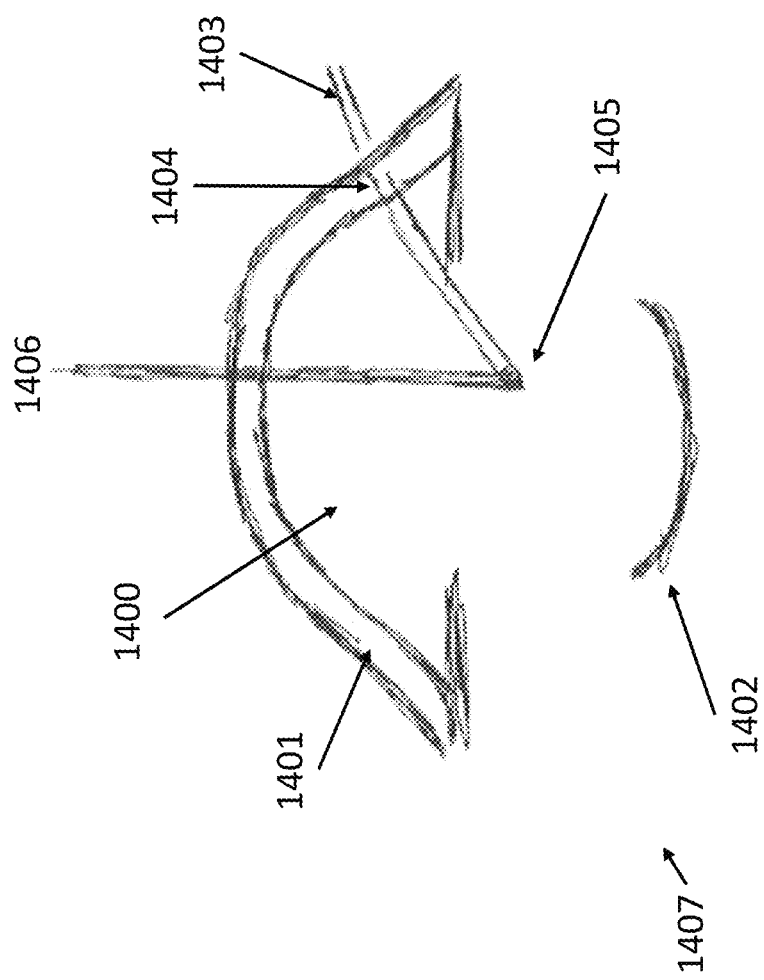
FIG. 14 is a diagram of a method of registration for tools and anatomical objects within the anterior chamber of an eye, according to certain embodiments of the present invention.

FIG. 14 illustrates a method of registration, the act of locating and tracking objects relative to a computer-generated map, for tools and anatomical objects within the anterior chamber 1400 of eye 1407, according to one embodiment of the present invention. Having inserted tool 1403 through an incision 1404 in the cornea 1401 in order to access a lens capsule 1402, the boundary and shape of the lens capsule 1402 may be captured to create a computer-generated map based on reflective portions of the lens capsule 1402.

In FIG. 14, OCT-based techniques may register the tool using the reflection signal 1406 from the reflective marker at the tool tip 1405 and the relative location of the tool base (not shown in FIG. 14). Using kinematics and reverse kinematics, the remaining portion of tool 1403, i.e., the shaft, may be computed based on the relative locations of the tool base and tool tip 1405. In OCT, the signals generate positional information in three dimensions. The reflective and refractive effects from the cornea and other optical surfaces may be compensated using optical de-warping. This form of registration, known as autocorrelation, starts by detecting signals at the tool tip based on the reflections from the reflective marks. Thus, using signals generated by this autocorrelation technique, the entire tool 1403 may be registered within the computer-generated map in Cartesian coordinates. Beyond OCT, other imaging modalities, including white light imaging and structured light imaging, can also be used to determine the location of the tool with respect to the anatomical features of the surgical field.

Figure 15:
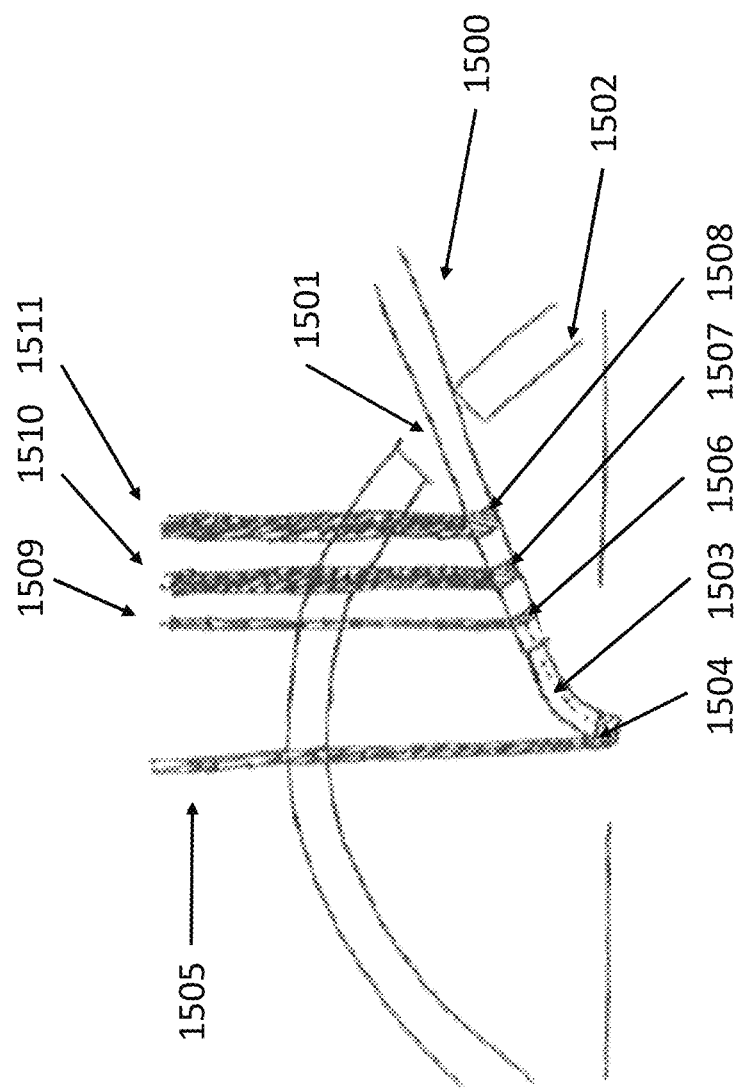
FIG. 15 is a diagram of a method of registration for non-linear tools and anatomical objects within a lens capsule, according to certain embodiments of the present invention.

FIG. 15 illustrates a method of registration for non-linear tools and anatomy within a lens capsule, according to an embodiment of the present invention. In FIG. 15, a tool 1500 inserted through an incision 1501 in the cornea 1502 with a pre-bent tip 1503 with a reflective marker 1504 to assist autocorrelation of the tool tip 1503. The autocorrelation signal of the tool tip 1503 based on the reflective marker 1504 is represented as a vertical, orthogonal line 1505 emanating from the reflective marker 1504. Reflective markers 1506, 1507, and 1508 may be present at predetermined intervals along the length of the tool 1500. Using kinematics and autocorrelation techniques for markers 1506, 1507, and 1508, the entire tool 1500 may be precisely registered within a computer-generated map in Cartesian (x-, y-, and z-) coordinates. Reflection signals 1509, 1510, and 1511 from markers 1505, 1506, and 1507 respectively may be used for registration.

Imaging techniques and sensors may also be used to optimize laser, flush, and aspiration parameters. For example, if it is detected that the tool tip 1503 is too close to anatomical structures, the laser power could be reduced to reduce the chance of injury. Similarly, flush and aspiration pressure may be manipulated to facilitate removal of the cataract material.

Figure 16:
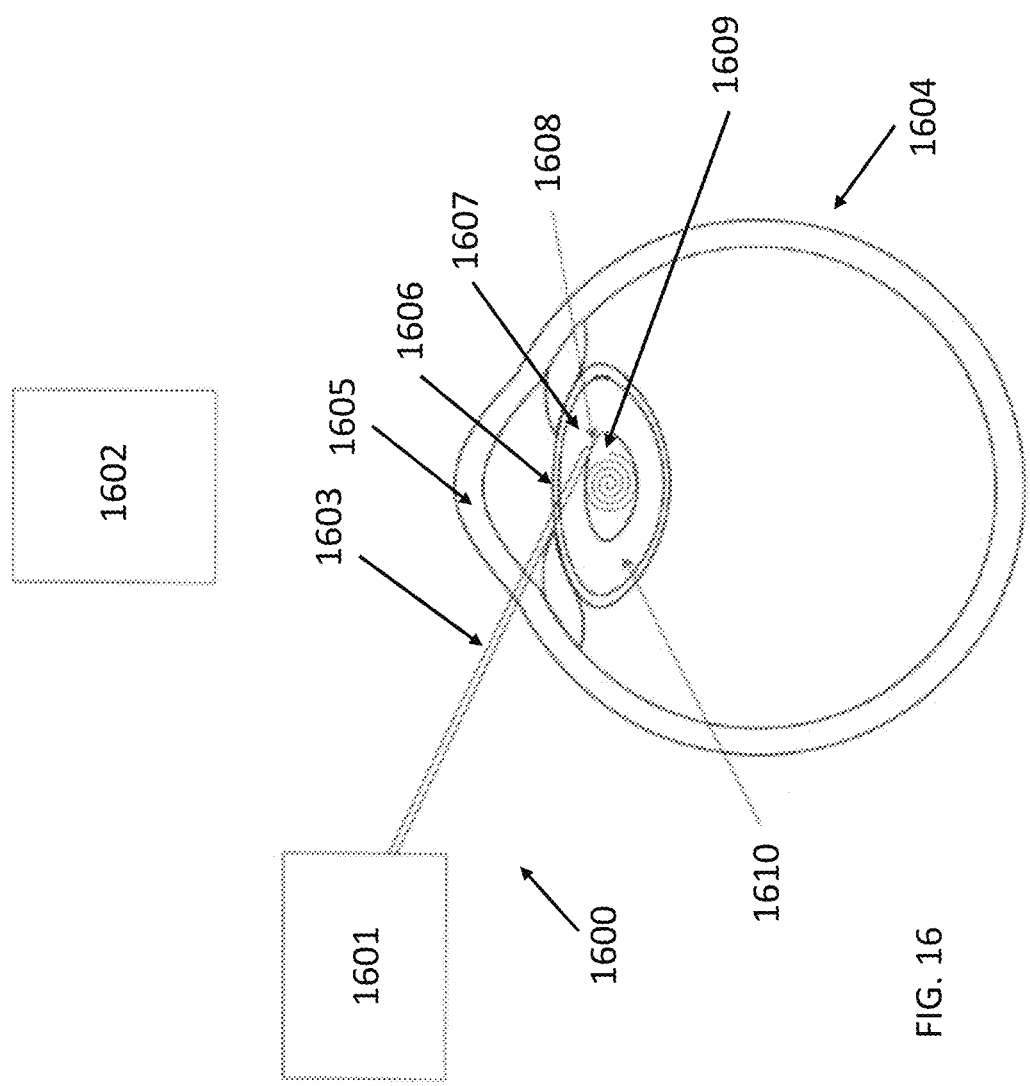
FIG. 16 is an illustration of a robotic laser tool that executes a preprogrammed spiral lasing pattern with the aid of a vision or OCT system, according to an embodiment of the present invention.

FIG. 16 illustrates an embodiment of the present invention executing a preprogrammed spiral lasing pattern with the aid of a vision, video or OCT system. In FIG. 16, a spiral tool path may be executed by a robotic system 1600 with a vision or OCT system 1602 and a robot arm 1601 that controls a laser tool 1603 that follows a tool path 1608 within the lens capsule 1606 in the eye 1604. Like FIG. 10, tool path 1608 starts in the center of the lens 1607 in the lens capsule 1606 in the nucleus 1609 and spirals outwards until it terminates near the cortex 1610.

In some embodiments, the imaging system can be traditional white light imaging and structured light imaging. In some embodiments, robotic controls sensitive to localization sensors and imaging may improve the safety of the tool and its ability to bound and calculate a preprogrammed lasing pattern to fit a particular patient profile.

FIG. 17 provides several diagrams where a lasing protocol manipulates the pulse repetition rate based on real-time information retrieved by a vision or OCT system in accordance with an embodiment of the present invention. In FIG. 17A, apparatus 1700 controls a robot tool 1701 with tool tip 1704 in response to control commands from a doctor 1705 on a robot master system 1702 and a vision or OCT system 1703. Tool tip 1704 may be manipulated by doctor 1705 over a tool path 1706 through the lens 1711 in the lens capsule 1710, the nucleus 1713, and lens cortex 1712 in a patient's eye 1707.

Figure 17A:
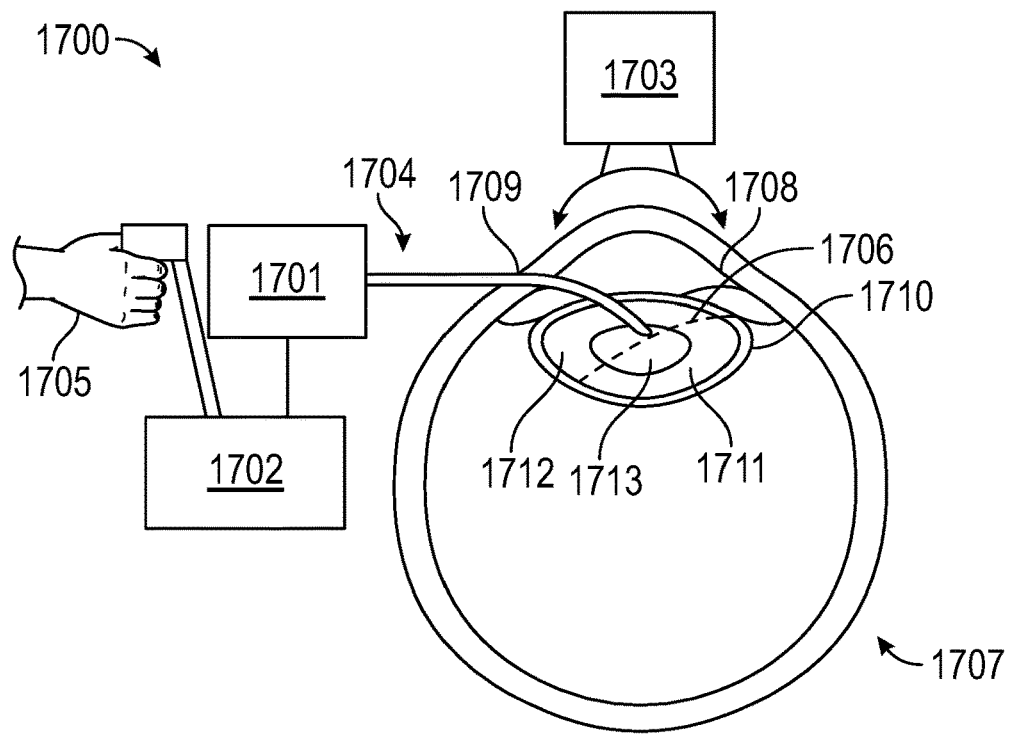
FIGS. 17A, 17B, 17C, and 17D are illustrations and charts showing the operation of a robotic laser device where a lasing protocol manipulates the pulse repetition rate based on real-time information retrieved by a vision or OCT system, according to an embodiment of the present invention.
Figure 17B:
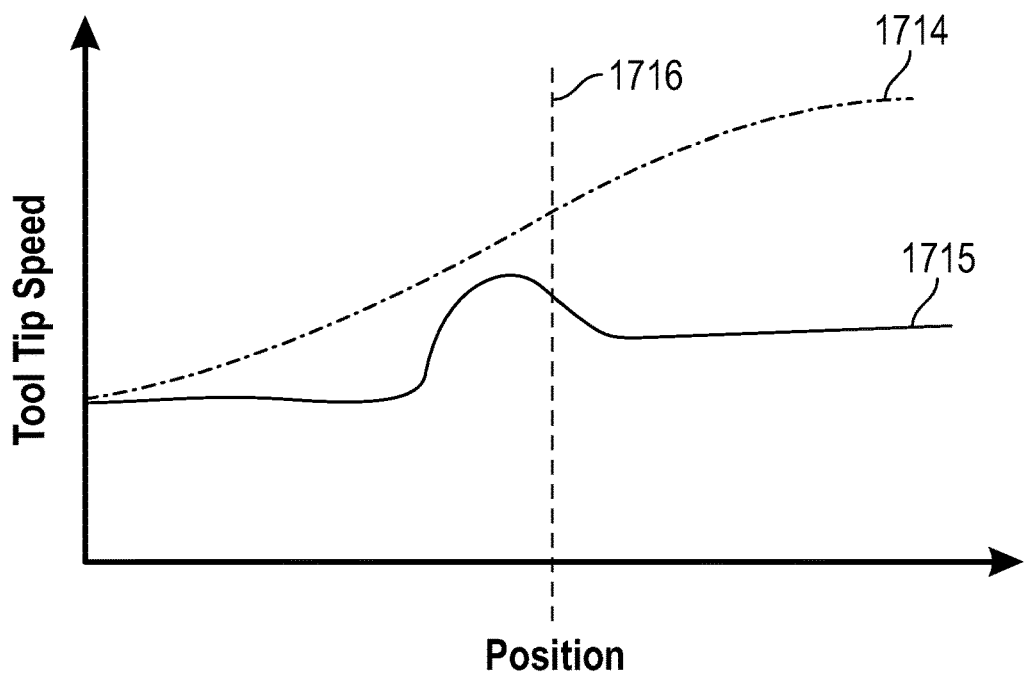

FIG. 17B provides a chart detailing how the tool tip 1704 and the patient's eye 1707 may move as the doctor maneuvers tool tip 1704 through tool path 1706. In FIG. 17B, line 1714 illustrates how tool tip speed varies as doctor 1705 commands the tool tip 1704 to maneuver along tool path 1706. In this example, rather than maneuver the tool tip 1704 at a steady speed, doctor 1705 increasingly maneuvers tool tip 1704 at a faster rate as it moves along the tool path 1706. Line 1715 illustrates how the eye 1707 moves as tool tip 1704 moves along tool path 1706. In this example, the patient's eye 1707 does not remain stationary, but moves as tool tip 1704 progresses down tool path 1706. Indeed, eye 1707 shifts immediately prior to tool 1704 reaching the lens nucleus 1713, represented by vertical dotted line 1716.

Figure 17C:
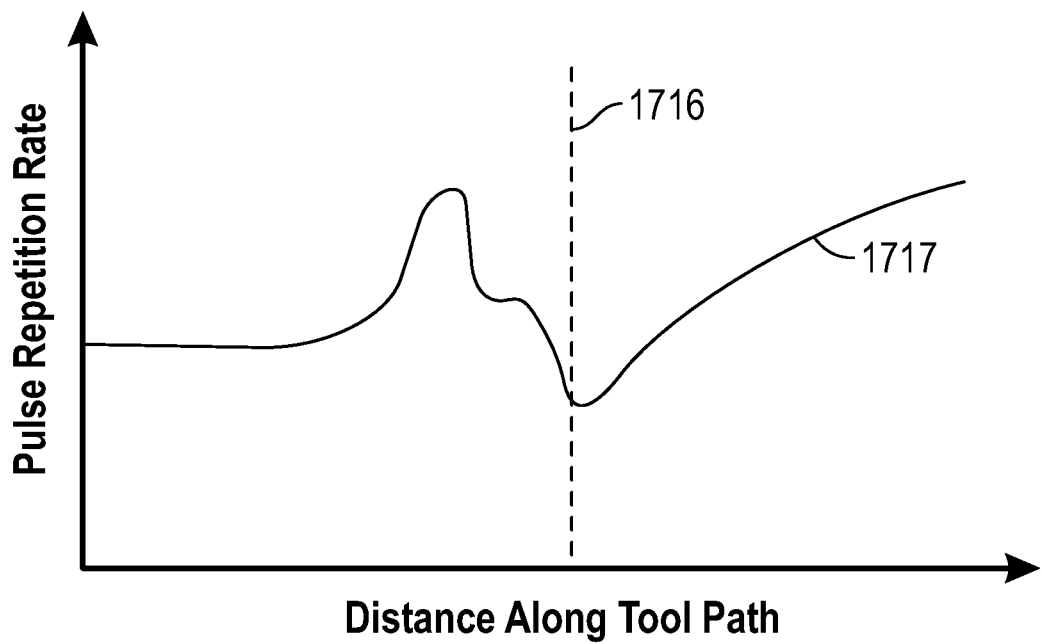

FIG. 17C provides a chart detailing how apparatus 1700 compensates for variations in tool tip speed 1714 and eye movement 1715 by altering pulse repetition rate in the laser in tool tip 1704. In FIG. 17C, line 1717 illustrates how apparatus 1700 varies the rate of pulse repetition of laser in tool tip 1704 as it traverses tool path 1706. As shown by line 1717, near the beginning of the tool path 1706, apparatus 1700 rapidly increases the pulse repetition rate when eye 1706 moves to create more exposure to lens cortex 1709. Conversely, as shown by the intersection of lines 1716 and 1717, when the tool tip 1704 coincides with the nucleus 1713, the pulse repetition rate quickly drops to address where the cataract is often hardest. Similar to the embodiment in FIG. 11, lower pulse repetition rate leads to greater laser pulse energy in the system of FIG. 17.

Figure 17D:
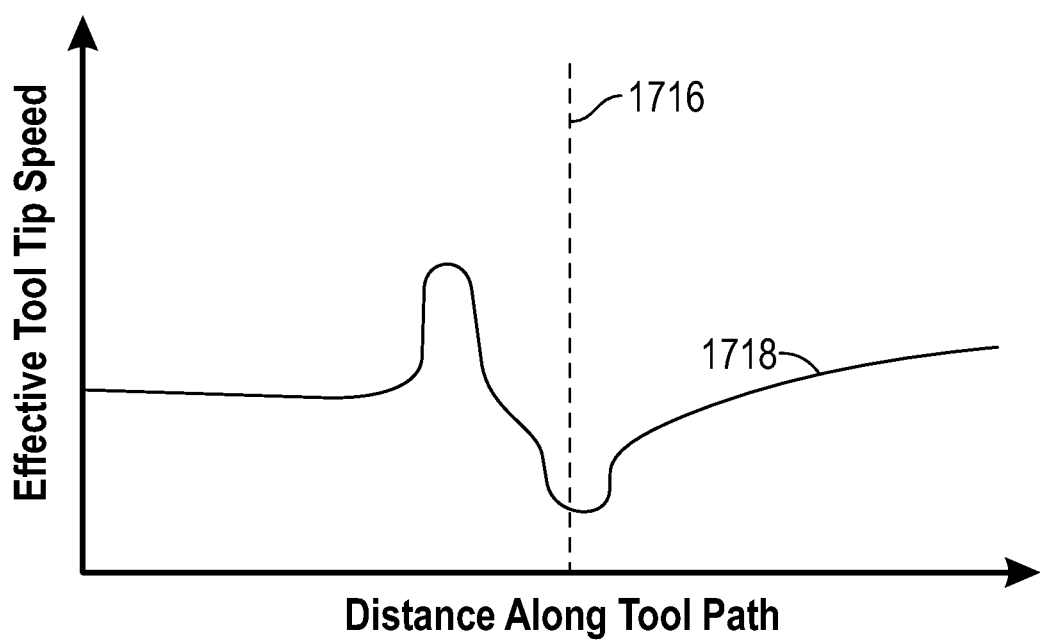

FIG. 17D provides a chart detailing how changes to the pulse repetition rate represented by line 1718 results in an "effective" tool tip speed that varies as tool tip 1704 traverses tool path 1706. Line 1718 illustrates how varying the pulse repetition rate of the laser in tool tip 1704 results in an effective tool speed, i.e., equivalent tool tip speed assuming a consistent pulse repetition rate. Consequently, use of vision or OCT systems 1703 allows apparatus 1700 to compensate for inconsistent tool tip speed and eye movement by altering the pulse rate repetition rate automatically in real-time. Accordingly, altering the pulse repetition rate has the same effect altering the tool tip speed, shown by line 1718 in FIG. 17D.

Tool Articulation

In some embodiments, the tool tip may sit in a robotically controlled articulating region. The articulation region may allow movement of the tip of the tool while avoiding motion in the rest of the tool. In some embodiments, the articulation region may include pre-bent tubes, pre-bent tubes recessed within straight or bent tubes, flexures with control wires, flexures fabricated with semiconductor fabrication technologies, and flexures with micro-motors and micro-gears. Use of a robotically controlled articulating tip minimizes the size of the incision in the lens capsule necessary to extract the cataract material. Hence, this is an important technology for capsulorhexis as will be discussed below.

An example of an articulating tool is an optical fiber encased in a pre-bent tube, where the pre-bent tube has a rigid, straight exterior tube. In some embodiments, the pre-bent tube can be retracted into the straight tube, creating a tool that can change from a bent to a straight configuration. The amount of retraction can be controlled robotically, allowing the bend on the tool to be synchronized with the tool pattern and or laser parameters. Use of a pre-bent tube does not limit the articulation means that can be used with the tool tip, other means include a flexure with one or more control wires.

Figure 18A:
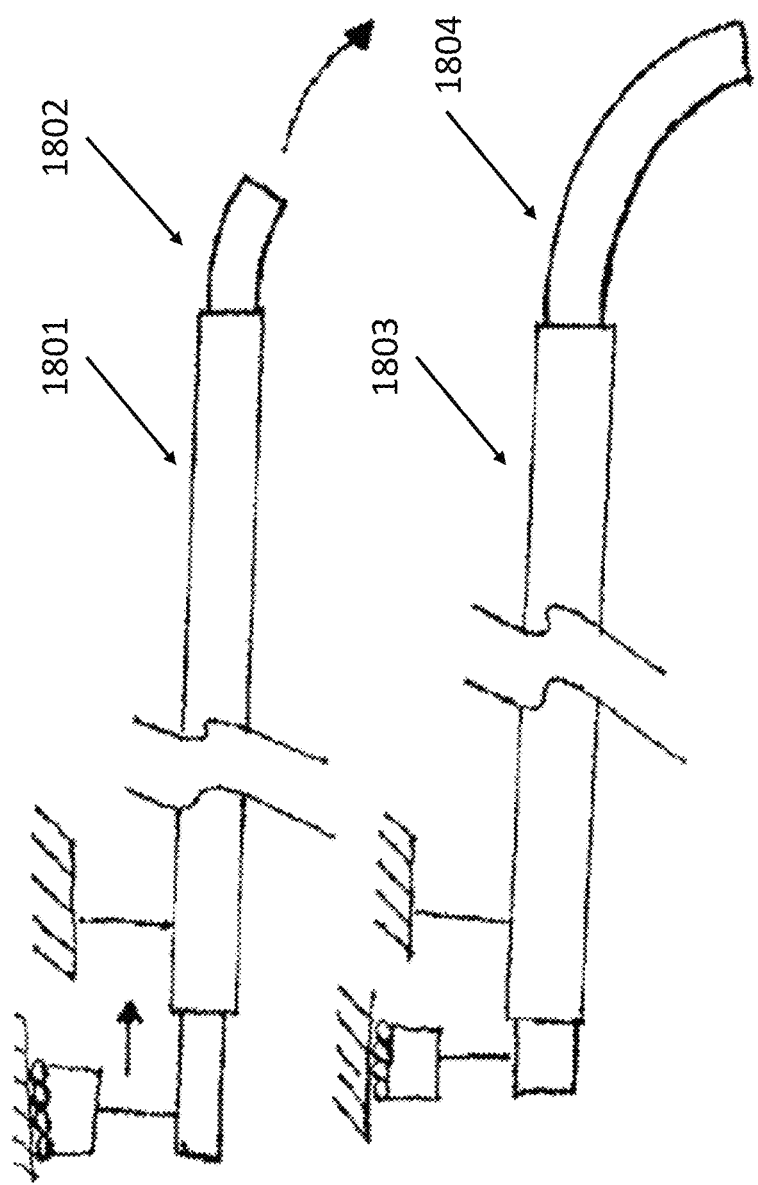
FIGS. 18A and 18B are illustrations of tool tip articulation according to certain embodiments of the present invention.
Figure 18B:
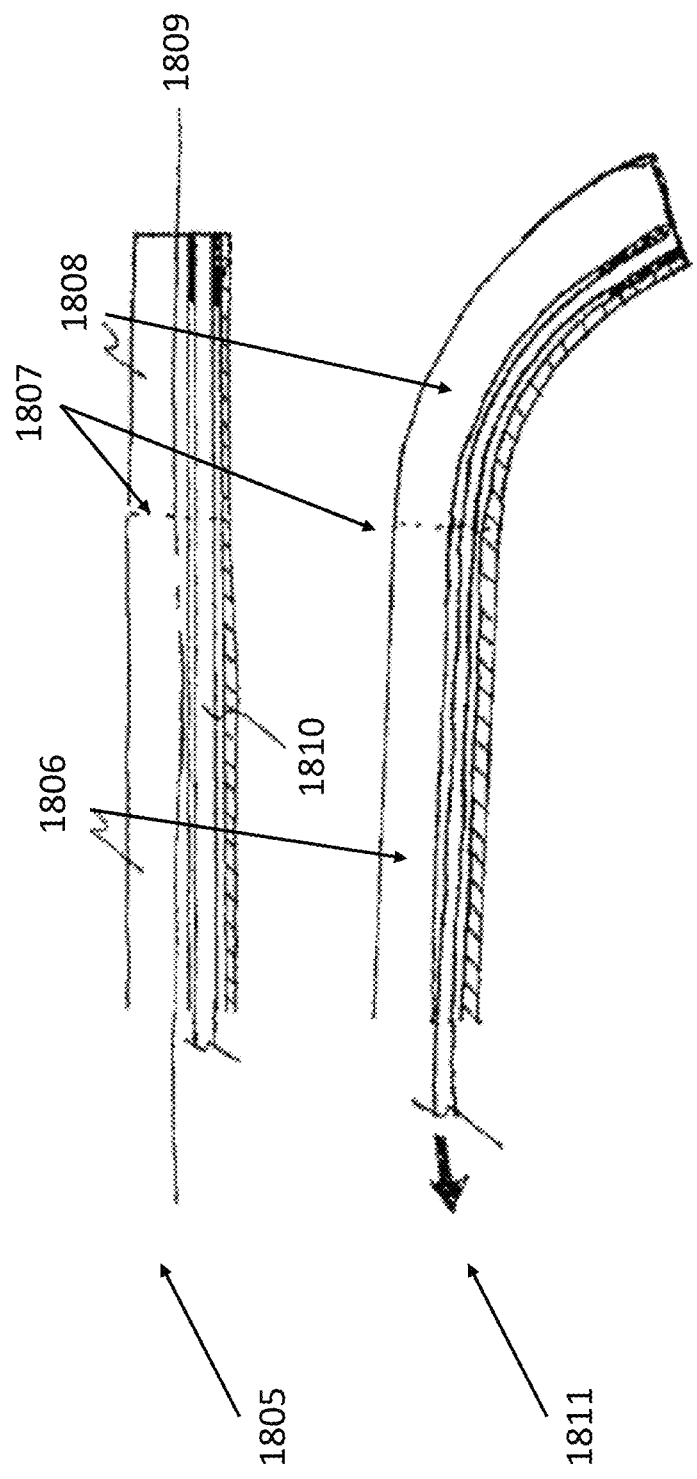

In some embodiments, the present invention may include a robot for positioning the tip of the tool in space and optionally providing for angular degrees of freedom for adjusting the direction of the laser tool. FIGS. 18A and 18B illustrates tool tip articulation in accordance with certain embodiments of the present invention. FIG. 18A illustrates concentric tube articulation as the pre-bent tool tips 1802 and 1804 extend from tools 1801 and 1803. As shown in FIG. 18A, the pre-bent tool tips 1802 and 1804 exhibit greater deviation from a neutral axis as they are extended a greater distance from tools 1801 and 1803.

FIG. 18B illustrates a detailed view of the tool tip articulation from the perspective of the laser fiber within the tool. As shown in tool tip 1805, a shaft 1806 may have an articulation point 1807 and a bend section 1808 beyond the articulation point 1807. When unbent, the shaft 1806 and bend section 1808 remain aligned around a neutral axis 1809. Similarly, a laser fiber 1810 fixedly coupled to tool tip 1805 would remain aligned around neutral axis 1809 when unbent. As shown in tool tip 1811, however, when articulated or bent, bend section 1808 may articulate beyond articulation point 1807.

Figure 19:
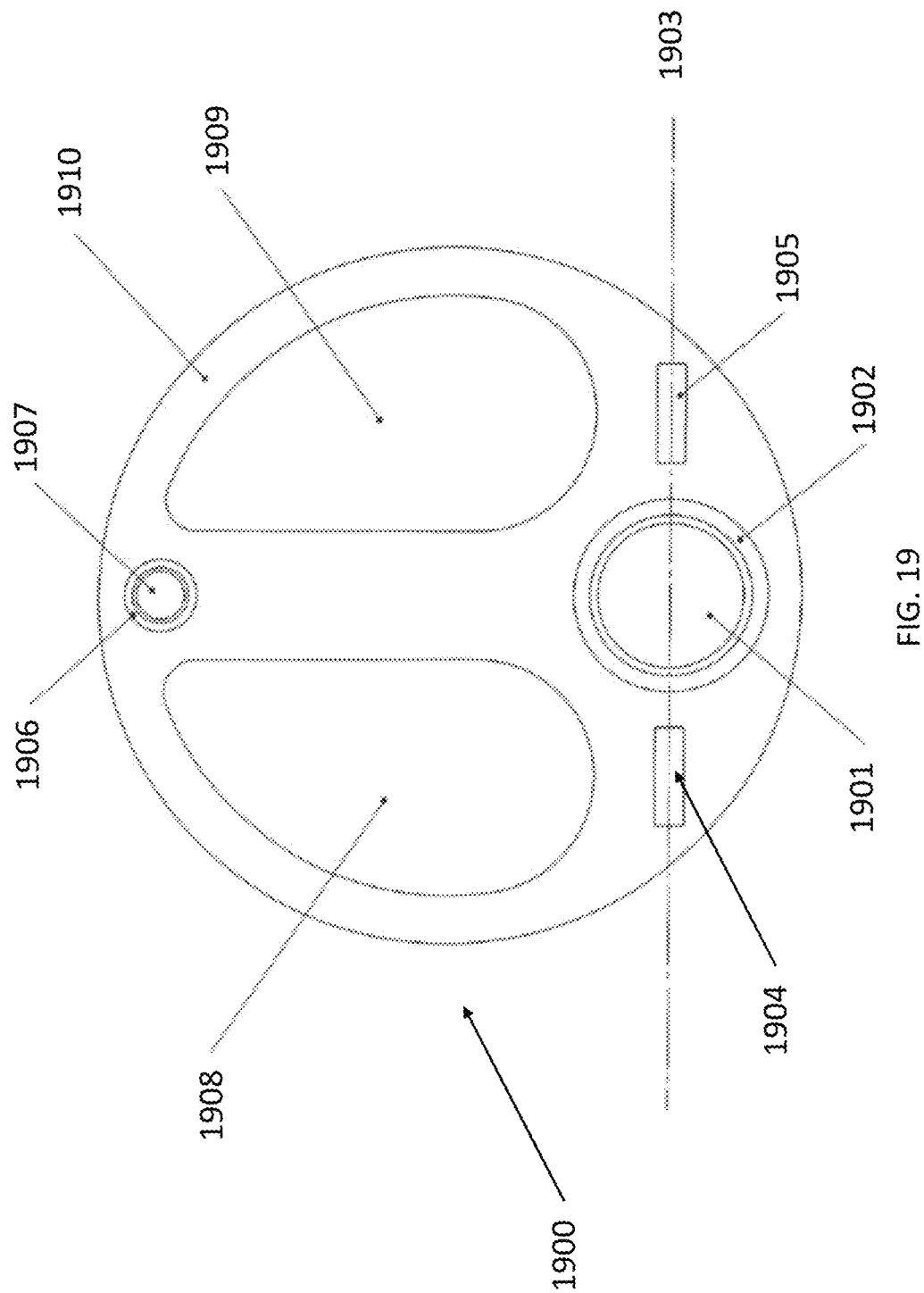
FIG. 19 is an illustration of a cross-sectional view of a one-way bending laser probe, according to an embodiment of the present invention.

FIG. 19 illustrates a cross-sectional view of a one-way bending laser probe, according to an embodiment of the present invention. In this embodiment, the tool 1900 includes a laser fiber 1901 within a laser lumen 1902. The tool's imaginary neutral axis 1903 runs through the laser lumen and the structural members 1904, 1905. Also, the tool 1900 contains a control lumen 1906 with a control tendon 1907, a flush lumen 1908, and an aspiration lumen 1909. A flexible extrusion 1910 is also included.

Figure 20:
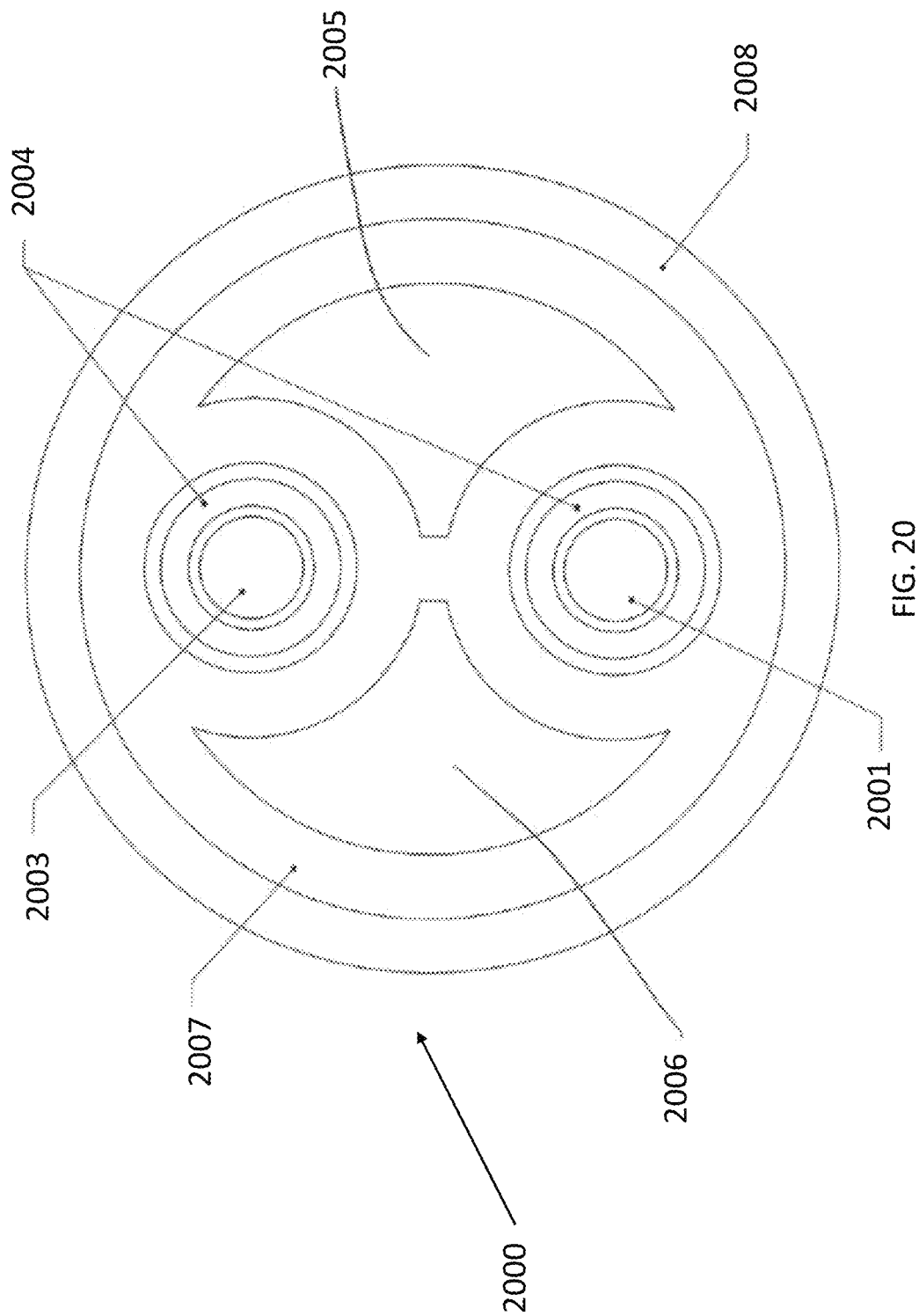
FIG. 20 is an illustration of a cross-sectional view of a concentric tube laser probe with OCT, according to an embodiment of the present invention.

FIG. 20 illustrates a cross-sectional view of a concentric tube laser probe with OCT, according to an embodiment of the present invention. In this embodiment, the tool 2000 includes a laser fiber 2001 surrounded by a polyimide liner 2002. Also, the tool 2000 contains an OCT fiber 2003 surrounded by a polyimide liner 2004, a flush lumen 2005, and an aspiration lumen 2006. A flexible multi-lumen extrusion 2007 and a formed deflectable tube 2008 surrounds the tool 2000 is also included.

Figure 21:
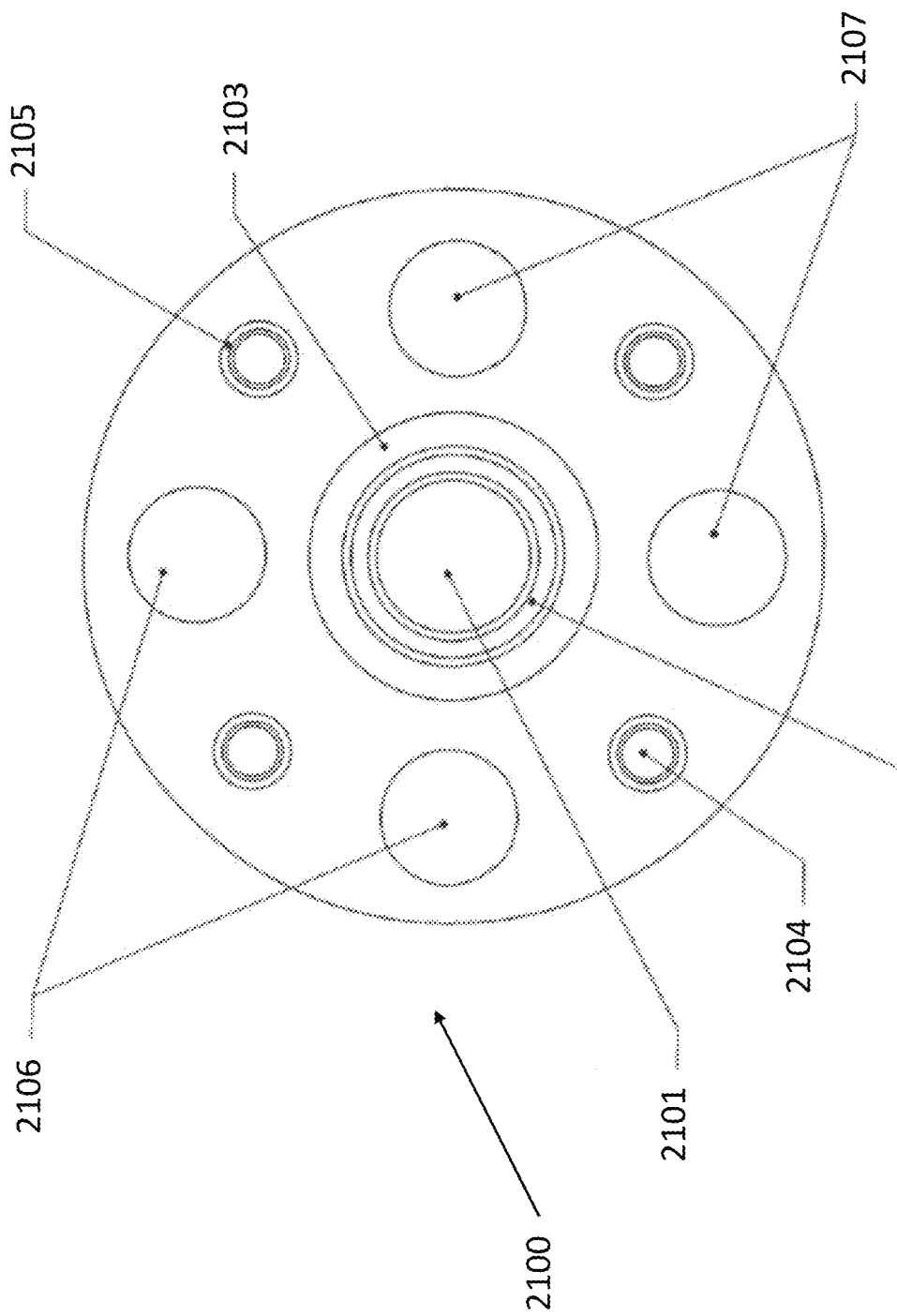
FIG. 21 is an illustration of a cross-sectional view of a four-way articulating tool, according to an embodiment of the present invention.

FIG. 21 illustrates a cross-sectional view of a four-way articulating tool, according to an embodiment of the present invention. In this embodiment, the articulating tool 2100 includes a laser fiber 2101 surrounded by a fiber jacket 2102, enclosed within a structural member 2103. As a four-way articulation tool, the tool 2100 contains a four control tendons, such as 2104, each enclosed by a tube member, such as 2105. The tool also contains a plurality of flush lumens 2106 and aspiration lumens 2107.

Applications for Capsulorhexis

Figure 22A:
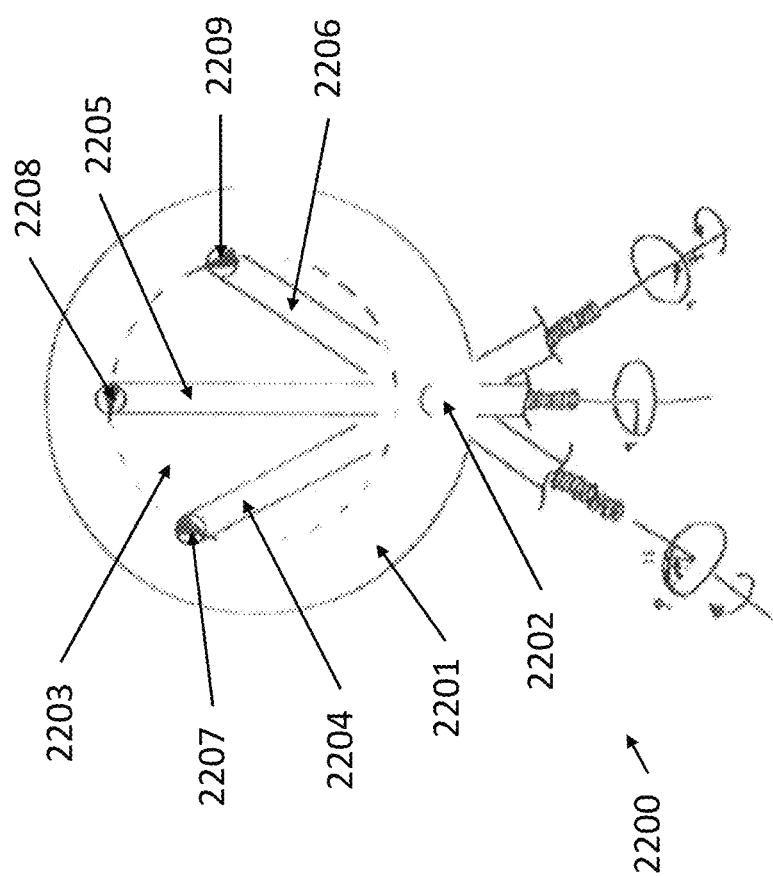

FIG. 22A and FIGS. 22B1-22B3 illustrate top-sectional views of a robotically controlled capsulorhexis procedure, according to two embodiments of the present invention. FIG. 22A specifically illustrates an embodiment of the invention where the tool tip (represented in several angles as 2204, 2205, 2206) may access different portions of the surface of the lens capsule 2203 by pivoting the tool tip from an incision 2202 in the cornea 2201 of the eye 2200. In FIG. 22A, the tool tip may be pivoted into a leftward position 2204 to make incisions on the left section 2207 of surface of the lens capsule 2203. In other circumstances, the tool tip may be directed straight (shown as 2205) at a diametrically opposed portion 2208 of the surface of the lens capsule 2203. In addition, the tool tip may be pivoted to access the right section 2209 of lens capsule 2203. A laser device may be coupled to the end of the tool tip in angles 2204, 2205, and 2206. In some embodiments, pivoting at incision 2202 allows for two part motion of the tool, including yaw and roll movement.

Figure 1:
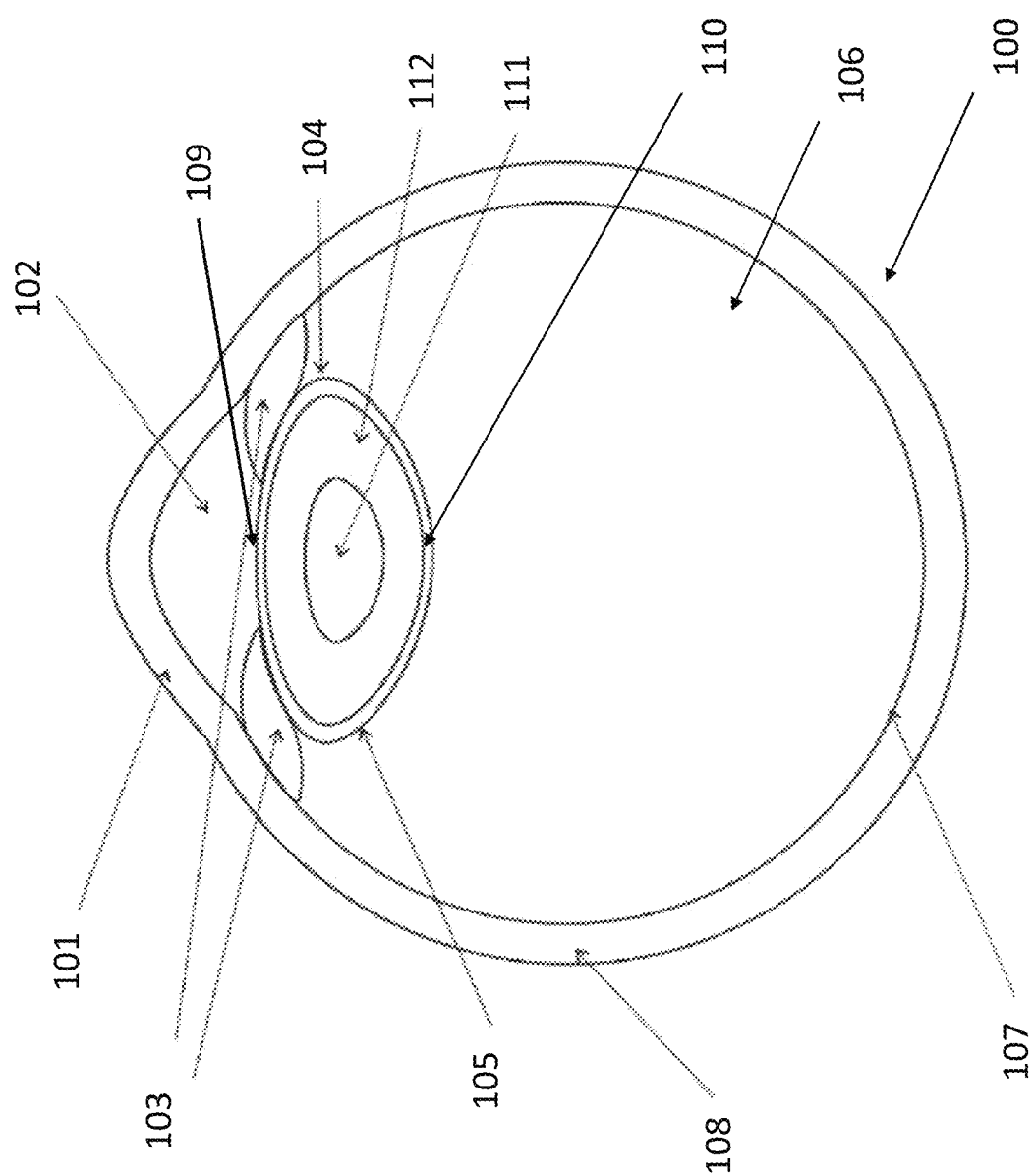
FIG. 1 is a diagram of the human eye, included for background.

FIGS. 22B1-22B3 illustrate top-sectional view of a robotically controlled capsulorhexis procedure using an embodiment of the present invention where shaped tubes, axially translatable to vary articulation angle, enable complex distal tip motion so that the tool tip may access different portions of the surface of a lens capsule.

As shown in scenario 2210, tool 2215 may be directed orthogonally towards the surface of lens capsule 2214 through an incision 2213 in the cornea 2212 in eye 2211. Having penetrated cornea 2212, tool tip 2216 may be extended from tool 2215 to target a diametrically opposed region 2217 on the surface of the lens capsule 2214. In scenario 2218, tube 2219 and tool tip 2216 may be manipulated to maneuver tool tip 2216 to target a right-side region 2220 of the surface of lens capsule 2214. Similarly, in scenario 2221, tube 2219 and tool tip 2216 may be manipulated to maneuver tool tip 2216 to target a left-side region 2222 of the surface of lens capsule 2214.

In some embodiments, a laser device may be coupled to the end of the tool tip 2216 in scenarios 2210, 2218, and 2221. In some embodiments, tube 2219 is constructed from pre-bent tubes from nitinol. In some embodiments, tube 2219 may be articulated using either pull wires, tendons, or cables. In some embodiments, the construction of tool 2215, tube 2219, and tool tip 2216 allows for roll motion, irrigation, and aspiration in both tube 2219 and tool tip 2216.

Instrument Drive Mechanisms

FIG. 23 illustrates an apparatus with an instrument drive mechanism to couple the tools described above to a robotic system, in accordance with an embodiment of the present invention. An instrument drive mechanism is a piece of mechanized equipment capable of driving an instrument or tool. In FIG. 23, the instrument drive mechanism 2302 is shown in a close view 2301 of the entire apparatus 2300. For this embodiment, the apparatus may be a robotic system with a proprietary instrument drive mechanism, such as the da Vinci® Surgical System by Intuitive Surgical, Incorporated, the Magellan™ Robotic System by Hansen Medical, Incorporated, the Micron by Carnegie Mellon University, or the Steady-Hand Eye Robot by John Hopkins University.

FIG. 24 illustrates a robotic apparatus with a plurality of instrument drive mechanisms and interfaces, in accordance with an embodiment of the present invention. In FIG. 24, the apparatus 2400 comprises two robotic arms, i.e., instrument drive mechanisms, identified as 2401 and 2402. Robotic arms 2401 and 2402 each have an individual instrument interface, shown as 2203 and 2204 respectively. Instrument interfaces 2203 and 2204 may each couple to a catheter-like tool, such as those discussed earlier.

In several embodiments of the present invention, the previously described tools—catheters, laser, OCT, flush and aspirations tools—may be controlled and coupled to the instrument drive mechanisms discussed in FIGS. 23 and 24 though instrument interfaces. Similarly, the components discussed with respect to FIGS. 13A, 13B, 13C, and 13D, such as flow rate meter, computer, feedback loop, pump, and pressure vessel, may be coupled to the robotic arm or instrument drive mechanisms discussed in FIGS. 23 and 24.

The present invention is not limited to embodiments using the aforementioned systems and the associated instrument drive mechanisms. One skilled in the art would appreciate modifications to facilitate coupling to different robotic arm configurations.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A method comprising:
   inserting a first tool into a chamber of a patient, the first tool comprising a plurality of lumens, wherein at least one of the plurality of lumens houses a laser fiber, wherein the first tool is attached to a first robotic arm;
   inserting a second tool into the chamber of the patient, the second tool comprising a flush and aspiration device, wherein the second tool is attached to a second robotic arm;
   articulating, via bending, a tip of the laser fiber separately from a tip of the first tool and applying laser energy from the laser fiber to break up an undesired clump of material into smaller pieces within the chamber of the patient;
   articulating, via bending, the second tool and aspirating and removing the smaller pieces from the chamber; and
   gradually varying a pulse repetition rate of the laser energy between a first value and a second value based on a distance that the tip of the first tool has traveled along a tool path, wherein the gradual varying of the pulse repetition rate is based on a hardness of the undesired clump of material at the distance along the tool path.

2. The method of claim 1, wherein the first tool comprises a fiber jacket that encloses the laser fiber.

3. The method of claim 2, wherein the first tool comprises four control tendons.

4. The method of claim 1, wherein the laser fiber is configured to extend beyond a length of a tip of the first tool.

5. The method of claim 1, wherein the second tool is dedicated only to flush and aspiration.

6. The method of claim 1, wherein the first tool and the second tool are articulated towards a same general location.

7. The method of claim 6, wherein at least one of the first tool and the second tool is angled from the top down and the other of the first tool and second tool is angled to undercut the undesired clump of material.

8. The method of claim 1, further comprising tracking the first tool to a computer generated map.

9. The method of claim 1, wherein the first tool comprises an electromagnetic (EM) sensor.

10. The method of claim 1, wherein the laser energy has a pulse energy, repetition rate and pulse duration that are controlled in real time.

11. The method of claim 1, wherein the second tool deploys a membrane umbrella.

12. The method of claim 1, further comprising articulating the tip of the first tool toward a nucleus of the undesired clump of material and slowing a speed of the tip of the first tool based on a distance between the tip of the first tool and the nucleus.

13. The method of claim 1, further comprising varying the pulse repetition rate of the laser energy between a first pulse repetition rate and a second pulse repetition rate that is higher than the first pulse repetition rate based on a distance between the tip of the first tool and the undesired clump of material.

14. The method of claim 1, wherein:
the second tool has a flush mechanism that operates via a pump that is controlled by a computer, and
the second tool has a flow rate meter that detects a velocity of liquid that exits the flush mechanism, wherein information regarding the velocity of the liquid can be sent to the computer, wherein the computer can change the velocity of the liquid.

15. The method of claim 1, wherein the laser fiber is aligned with a neutral axis of the first tool.

16. The method of claim 1, wherein the tool path traverses the undesired clump of material.

17. A method comprising:
inserting a first tool into a chamber of a patient, the first tool comprising a plurality of lumens, wherein at least one of the plurality of lumens houses a laser fiber, wherein the first tool is attached to a first robotic arm;
inserting a second tool into the chamber of the patient, the second tool comprising a flush and aspiration device, wherein the second tool is attached to a second robotic arm;
articulating, via bending, a tip of the laser fiber separately from a tip of the first tool and applying laser energy from the laser fiber to break up an undesired clump of material into smaller pieces within the chamber of the patient;
articulating, via bending, the second tool and aspirating and removing the smaller pieces from the chamber; and
gradually varying a pulse repetition rate of the laser energy between a first value and a second value based on a distance that the tip of the first tool has traveled along a tool path, wherein the gradual varying of the pulse repetition rate further comprises compensating for inconsistencies in a speed of the tip of the first tool and compensating for movement of an anatomical structure of the patient.

18. A method comprising:
inserting a first tool into a chamber of a patient, the first tool comprising a plurality of lumens, wherein at least one of the plurality of lumens houses a laser fiber, wherein the first tool is attached to a first robotic arm;
inserting a second tool into the chamber of the patient, the second tool comprising a flush and aspiration device, wherein the second tool is attached to a second robotic arm;
articulating, via bending, a tip of the laser fiber separately from a tip of the first tool and applying laser energy from the laser fiber to break up an undesired clump of material into smaller pieces within the chamber of the patient;
articulating, via bending, the second tool and aspirating and removing the smaller pieces from the chamber; and
gradually varying a pulse repetition rate of the laser energy between a first value and a second value based on a distance that the tip of the first tool has traveled along a tool path, wherein the gradual varying of the pulse repetition rate further comprises achieving an effective tool tip speed that is substantially equivalent to a speed of the tip of the first tool having a consistent pulse repetition rate.

19. A method comprising:
inserting a first tool into a chamber of a patient, the first tool comprising a plurality of lumens, wherein at least one of the plurality of lumens houses a laser fiber, wherein the first tool is attached to a first robotic arm;
inserting a second tool into the chamber of the patient, the second tool comprising a flush and aspiration device, wherein the second tool is attached to a second robotic arm;
bending a tip of the laser fiber separately from a tip of the first tool and applying laser energy from the laser fiber to break up an undesired clump of material into smaller pieces within the chamber of the patient;
bending the second tool and aspirating and removing the smaller pieces from the chamber; and
varying a pulse repetition rate of the laser energy based on a signal received from an optical sensor as the tip of the first tool has traveled along a tool path, wherein the pulse repetition rate is varied based on a speed of the tip of the first tool, movement of an anatomical structure of the patient, and a distance that the tip of the first tool has traveled along a tool path.

* * * * *